United States Patent
Tehrani (12)

(10) Patent No.: US 10,857,363 B2
(45) Date of Patent: Dec. 8, 2020

(54) DEVICES AND METHODS FOR REDUCING INTRATHORACIC PRESSURE

(71) Applicant: RMX, LLC, San Francisco, CA (US)

(72) Inventor: Amir J. Tehrani, San Francisco, CA (US)

(73) Assignee: RMX, LLC, San Francisco, CA (US)

( * ) Notice: Subject to any disclaimer, the term of this patent is extended or adjusted under 35 U.S.C. 154(b) by 0 days.

(21) Appl. No.: 15/424,253

(22) Filed: Feb. 3, 2017

(65) Prior Publication Data

US 2017/0143973 A1   May 25, 2017

Related U.S. Application Data

(63) Continuation of application No. PCT/US2015/047042, filed on Aug. 26, 2015.

(60) Provisional application No. 62/041,987, filed on Aug. 26, 2014.

(51) Int. Cl.
    *A61N 1/36* (2006.01)
    *A61N 1/365* (2006.01)
    *A61N 1/362* (2006.01)

(52) U.S. Cl.
    CPC ....... *A61N 1/36139* (2013.01); *A61N 1/3601* (2013.01); *A61N 1/3627* (2013.01); *A61N 1/36053* (2013.01); *A61N 1/36057* (2013.01); *A61N 1/36114* (2013.01); *A61N 1/36117* (2013.01); *A61N 1/36514* (2013.01); *A61N 1/36521* (2013.01)

(58) Field of Classification Search
    CPC .............. A61N 1/36139; A61N 1/3601; A61N 1/36053; A61N 1/36057; A61N 1/3606; A61N 1/36114; A61N 1/36117
    See application file for complete search history.

(56) References Cited

U.S. PATENT DOCUMENTS

| | | | |
|---|---|---|---|
| 3,773,051 | A | 11/1973 | Holcomb et al. |
| 4,827,935 | A | 5/1989 | Geddes et al. |
| 4,830,008 | A | 5/1989 | Meer |
| 5,056,519 | A | 10/1991 | Vince |
| 5,146,918 | A | 9/1992 | Kallok et al. |
| 5,174,287 | A | 12/1992 | Kallok et al. |
| 5,190,036 | A | 3/1993 | Linder |
| 5,211,173 | A | 5/1993 | Kallok et al. |

(Continued)

FOREIGN PATENT DOCUMENTS

| DE | 112004001957 T5 | 8/2006 |
|---|---|---|
| DE | 112004001953 T5 | 10/2006 |

(Continued)

OTHER PUBLICATIONS

"Quadripolar Pacing Addresses Issues Without Moving Leads," *Diagnostic & Invasive Cardiology*, 1 page, Jun. 1, 2010, Scranton Gillette Communications.

(Continued)

*Primary Examiner* — Paula J Stice
(74) *Attorney, Agent, or Firm* — Levine Bagade Han LLP

(57) ABSTRACT

Devices and methods are provided to treat acute and chronic heart failure by using one or more implantable or non-implantable sensors along with phrenic nerve stimulation to reduce intrathoracic pressure and thereby reduce pulmonary artery, atrial, and ventricular pressures leading to reduced complications and hospitalization.

22 Claims, 8 Drawing Sheets

(56) References Cited

U.S. PATENT DOCUMENTS

| | | |
|---|---|---|
| 5,215,082 A | 6/1993 | Kallok et al. |
| 5,233,983 A | 8/1993 | Markowitz |
| 5,265,604 A | 11/1993 | Vince |
| 5,281,219 A | 1/1994 | Kallok |
| 5,300,094 A | 4/1994 | Kallok et al. |
| 5,423,327 A | 6/1995 | Clauson et al. |
| 5,483,969 A | 1/1996 | Testerman et al. |
| 5,485,851 A | 1/1996 | Erickson |
| 5,522,862 A | 6/1996 | Testerman et al. |
| 5,524,632 A | 6/1996 | Stein et al. |
| 5,540,731 A | 7/1996 | Testerman |
| 5,540,732 A | 7/1996 | Testerman |
| 5,540,733 A | 7/1996 | Testerman et al. |
| 5,546,952 A | 8/1996 | Erickson |
| 5,549,655 A | 8/1996 | Erickson |
| 5,572,543 A | 11/1996 | Heinemann et al. |
| 5,678,535 A | 10/1997 | DiMarco |
| 5,766,228 A | 6/1998 | Bonnet et al. |
| 5,797,923 A | 8/1998 | Aiyar et al. |
| 5,800,470 A | 9/1998 | Stein et al. |
| 5,814,086 A | 9/1998 | Hirschberg et al. |
| 5,830,008 A | 11/1998 | Broschard, III |
| 5,876,353 A | 3/1999 | Riff |
| 5,895,360 A | 4/1999 | Christopherson et al. |
| 5,911,218 A | 6/1999 | DiMarco |
| 5,944,680 A | 8/1999 | Christopherson et al. |
| 6,021,352 A | 2/2000 | Christopherson et al. |
| 6,099,479 A | 8/2000 | Christopherson et al. |
| 6,212,435 B1 | 4/2001 | Lattner et al. |
| 6,224,562 B1 | 5/2001 | Lurie et al. |
| 6,251,126 B1 | 6/2001 | Ottenhoff et al. |
| 6,269,269 B1 | 7/2001 | Ottenhoff et al. |
| 6,312,399 B1 | 11/2001 | Lurie et al. |
| 6,314,324 B1 | 11/2001 | Lattner et al. |
| 6,345,202 B2 | 2/2002 | Richmond et al. |
| 6,357,438 B1 | 3/2002 | Hansen |
| 6,415,183 B1 | 7/2002 | Scheiner et al. |
| 6,463,327 B1 | 10/2002 | Lurie et al. |
| 6,480,733 B1 | 11/2002 | Turcott |
| 6,489,447 B1 | 12/2002 | Basey et al. |
| 6,512,949 B1 | 1/2003 | Combs et al. |
| 6,527,729 B1 | 3/2003 | Turcott |
| 6,542,774 B2 | 4/2003 | Hill et al. |
| 6,572,543 B1 | 6/2003 | Christopherson et al. |
| 6,574,507 B1 | 6/2003 | Bonnet |
| 6,587,725 B1 | 7/2003 | Durand et al. |
| 6,587,726 B2 | 7/2003 | Lurie et al. |
| 6,589,188 B1 | 7/2003 | Street et al. |
| 6,600,949 B1 | 7/2003 | Turcott |
| 6,633,779 B1 | 10/2003 | Schuler et al. |
| 6,651,652 B1 | 11/2003 | Ward |
| 6,731,984 B2 | 5/2004 | Cho et al. |
| 6,735,479 B2 | 5/2004 | Fabian et al. |
| 6,752,765 B1 | 6/2004 | Strobel et al. |
| 6,770,022 B2 | 8/2004 | Mechlenburg et al. |
| 6,811,537 B2 | 11/2004 | Bardy |
| 6,830,548 B2 | 12/2004 | Bonnet et al. |
| 6,881,192 B1 | 4/2005 | Park |
| 6,908,437 B2 | 6/2005 | Bardy |
| 7,058,453 B2 | 6/2006 | Nelson et al. |
| 7,070,568 B1 | 7/2006 | Koh et al. |
| 7,082,331 B1 | 7/2006 | Park et al. |
| 7,117,032 B2 | 10/2006 | Childre et al. |
| 7,277,757 B2 | 10/2007 | Casavant et al. |
| 7,532,934 B2 | 5/2009 | Lee et al. |
| 7,610,094 B2 | 10/2009 | Stahmann et al. |
| 7,840,270 B2 | 11/2010 | Ignagni et al. |
| 7,970,475 B2 | 6/2011 | Tehrani et al. |
| 7,979,128 B2 | 7/2011 | Tehrani et al. |
| 8,116,872 B2 | 2/2012 | Tehrani et al. |
| 8,140,164 B2 | 3/2012 | Tehrani et al. |
| 8,160,711 B2 | 4/2012 | Tehrani et al. |
| 8,200,336 B2 | 6/2012 | Tehrani et al. |
| 8,244,358 B2 | 8/2012 | Tehrani et al. |
| 8,255,056 B2 | 8/2012 | Tehrani |
| 8,265,759 B2 | 9/2012 | Tehrani et al. |
| 8,280,513 B2 | 10/2012 | Tehrani et al. |
| 8,335,567 B2 | 12/2012 | Tehrani et al. |
| 8,348,941 B2 | 1/2013 | Tehrani |
| 8,412,331 B2 | 4/2013 | Tehrani et al. |
| 8,467,876 B2 | 6/2013 | Tehrani |
| 8,509,901 B2 | 8/2013 | Tehrani |
| 9,259,573 B2 | 2/2016 | Tehrani et al. |
| 9,370,657 B2 | 6/2016 | Tehrani et al. |
| 10,518,090 B2* | 12/2019 | Gelfand ............... A61B 5/0816 |
| 2002/0049482 A1 | 4/2002 | Fabian et al. |
| 2002/0188332 A1* | 12/2002 | Lurie ..................... A61H 31/00 607/48 |
| 2002/0193697 A1 | 12/2002 | Cho et al. |
| 2002/0193839 A1 | 12/2002 | Cho et al. |
| 2003/0127091 A1 | 7/2003 | Chang |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0195571 A1 | 10/2003 | Burnes et al. |
| 2003/0204213 A1 | 10/2003 | Jensen et al. |
| 2003/0225339 A1 | 12/2003 | Orr et al. |
| 2004/0044377 A1 | 3/2004 | Larsson |
| 2004/0059240 A1 | 3/2004 | Cho et al. |
| 2004/0077953 A1 | 4/2004 | Turcott |
| 2004/0088015 A1* | 5/2004 | Casavant ............ A61N 1/3601 607/14 |
| 2004/0111040 A1 | 6/2004 | Ni et al. |
| 2004/0116784 A1 | 6/2004 | Gavish |
| 2004/0122484 A1 | 6/2004 | Hatlestad et al. |
| 2004/0134496 A1 | 7/2004 | Cho et al. |
| 2004/0138719 A1 | 7/2004 | Cho et al. |
| 2004/0176809 A1 | 9/2004 | Cho et al. |
| 2004/0199221 A1 | 10/2004 | Fabian et al. |
| 2004/0225226 A1 | 11/2004 | Lehrman et al. |
| 2004/0237963 A1 | 12/2004 | Berthon-Jones |
| 2005/0021102 A1 | 1/2005 | Ignagni et al. |
| 2005/0039745 A1 | 2/2005 | Stahmann et al. |
| 2005/0043644 A1 | 2/2005 | Stahmann et al. |
| 2005/0043772 A1 | 2/2005 | Stahmann et al. |
| 2005/0055060 A1 | 3/2005 | Koh et al. |
| 2005/0061315 A1 | 3/2005 | Lee et al. |
| 2005/0061319 A1 | 3/2005 | Hartley et al. |
| 2005/0061320 A1 | 3/2005 | Lee et al. |
| 2005/0065563 A1 | 3/2005 | Scheiner |
| 2005/0065567 A1 | 3/2005 | Lee et al. |
| 2005/0074741 A1 | 4/2005 | Lee et al. |
| 2005/0076909 A1 | 4/2005 | Stahmann et al. |
| 2005/0080461 A1 | 4/2005 | Stahmann et al. |
| 2005/0085734 A1 | 4/2005 | Tehrani |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0101833 A1 | 5/2005 | Hsu et al. |
| 2005/0107860 A1 | 5/2005 | Ignagni et al. |
| 2005/0115561 A1 | 6/2005 | Stahmann et al. |
| 2005/0119711 A1 | 6/2005 | Cho et al. |
| 2005/0145246 A1 | 7/2005 | Hartley et al. |
| 2005/0148897 A1 | 7/2005 | Cho et al. |
| 2005/0165457 A1 | 7/2005 | Benser et al. |
| 2005/0224076 A1 | 10/2005 | Pflichner et al. |
| 2005/0240240 A1 | 10/2005 | Park et al. |
| 2005/0261600 A1 | 11/2005 | Aylsworth |
| 2005/0261747 A1 | 11/2005 | Schuler et al. |
| 2006/0030894 A1 | 2/2006 | Tehrani |
| 2006/0036294 A1 | 2/2006 | Tehrani |
| 2006/0058852 A1 | 3/2006 | Koh et al. |
| 2006/0064030 A1 | 3/2006 | Cosentino et al. |
| 2006/0064325 A1 | 3/2006 | Matsumoto et al. |
| 2006/0122622 A1 | 6/2006 | Truckai et al. |
| 2006/0122661 A1 | 6/2006 | Mandell |
| 2006/0122662 A1 | 6/2006 | Tehrani |
| 2006/0142815 A1 | 6/2006 | Tehrani et al. |
| 2006/0149334 A1 | 7/2006 | Tehrani et al. |
| 2006/0155341 A1 | 7/2006 | Tehrani et al. |
| 2006/0167523 A1 | 7/2006 | Tehrani et al. |

(56) References Cited

U.S. PATENT DOCUMENTS

| | | |
|---|---|---|
| 2006/0224211 A1 | 10/2006 | Durand et al. |
| 2006/0247729 A1 | 11/2006 | Tehrani et al. |
| 2006/0282131 A1 | 12/2006 | Caparso et al. |
| 2007/0021795 A1 | 1/2007 | Tehrani |
| 2007/0156199 A1 | 7/2007 | Koh et al. |
| 2008/0021506 A1 | 1/2008 | Grocela |
| 2008/0109047 A1 | 5/2008 | Pless |
| 2008/0154330 A1 | 6/2008 | Tehrani et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183239 A1 | 7/2008 | Tehrani et al. |
| 2008/0183240 A1 | 7/2008 | Tehrani et al. |
| 2008/0188903 A1 | 8/2008 | Tehrani et al. |
| 2008/0188904 A1 | 8/2008 | Tehrani et al. |
| 2008/0208281 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2011/0230932 A1 | 9/2011 | Tehrani et al. |
| 2011/0288609 A1 | 11/2011 | Tehrani et al. |
| 2012/0053654 A1 | 3/2012 | Tehrani et al. |
| 2012/0109249 A1 | 5/2012 | Tehrani et al. |
| 2012/0158091 A1 | 6/2012 | Tehrani et al. |
| 2012/0323293 A1 | 12/2012 | Tehrani et al. |
| 2013/0197601 A1 | 8/2013 | Tehrani et al. |
| 2013/0296964 A1 | 11/2013 | Tehrani |
| 2013/0296973 A1 | 11/2013 | Tehrani et al. |
| 2015/0034081 A1 | 2/2015 | Tehrani et al. |
| 2017/0036017 A1 | 2/2017 | Tehrani et al. |

FOREIGN PATENT DOCUMENTS

| | | |
|---|---|---|
| DE | 112004001954 T5 | 10/2006 |
| WO | WO 1986/000234 | 1/1986 |
| WO | WO 2005/037077 | 4/2005 |
| WO | WO 2005/037172 | 4/2005 |
| WO | WO 2005/037173 | 4/2005 |
| WO | WO 2005/037174 | 4/2005 |
| WO | WO 2005/037220 | 4/2005 |
| WO | WO 2005/037366 | 4/2005 |
| WO | WO 2007/058938 | 5/2007 |
| WO | WO 2016/033245 | 3/2016 |

OTHER PUBLICATIONS

Abraham, W., "Advances in Heart Failure Therapy in the Primary Care Context," *Medscape Family Medicine/Primary Care,* 7 pages, 2004.

Aiyar, H. et al, "Laparoscopic Implant, Device for Intermuscular Electrodes," *IEEE-EMBC and CMBCC,* pp. 1167-1168, 1995.

Aiyar, H. et al, "Laparoscopic Implant Instrument for the Placement of Intramuscular Electrodes in the Diaphragm," *Transactions on Rehabilitation Engineering,* pp. 360-371, Sep. 1999.

Arzt, M. et al, "Treatment of Sleep Apnea in Heart Failure," *AJRCCM,* 36 pages, Mar. 9, 2006.

Azevedo, ER et al. Reducing Cardiac Filling Pressure Lowers Norepinephrine Spillover in 12, 22 Patients With Chronic Heart Failure. Circulation. May 2, 2000, vol. 101; DOI. 1 0.1161/CIR.1 01.17 .2053; pp. 2053-2059; p. 2057, paragraph 2; p. 2058, paragraph 3.

Bernardi, L. et al, "Effect of Rosary Prayer and Yoga Mantras on Autonomic Cardiovascular Rhythms: Comparative Study," *BMJ,* 323:22-29, Dec. 2001.

Bernardi, L. et al, "Slow Breathing Increases Arterial Baroreflex sensitivity in Patients with Chronic Heart Failure," *Circulation,* 105;143-145, 2002, *American Heart Association.*

Bocchiardo, Mario et al., "Iintracardiac impedance monitors stroke volume in resynchronization therapy patients", Europace, 12:702-707, 2010.

Boston Scientific, "Diaphragm Stimulation During Daily LV Lead Impedance Measurements", Product Education Brochure, 2 pages, Sep. 26, 2008.

Bradley, T.D. et al, "Sleep Apnea and Heart Failure, Part I. Obstructive Sleep Apnea," *Circulation,* pp. 1671-1678, Apr. 1, 2003.

Chaturvedi, Rakesh K., et al., "Use of Negative Extrathoracic Pressure to Improve Hemodynamics After Cardiac Surgery", Ann Thorac Surg, 85:1355-60, 2008.

DiMarco, A F., "Combined Intercostal and Diaphragm Pacing to Provide Artificial Ventilation in Patients With Tetraplegia" *Arch Phys Med Rehabil,* vol. (86), pp. 1200-1207, 2005.

DiMarco, A. F. et al, "Phrenic Nerve Pacing in a Tetraplegic Patient via Intramuscular Diaphragm Electrodes," *American Journal of Respiratory and Critical Care Medicine,* 144:1604-1606, 2002.

Dunn, R., "Diaphragm and Accessory Respiratory Muscle Stimulation Using Intramuscular Electrodes" *Arch Phys Med Rehabil,* vol. (76), pp. 266-271, 1995.

Fessler, H.E., "Heart-Lung Interactions: Applications in the Critically Ill" *Eur. Respir. J.,* vol. 10, pp. 226-237, 1997.

Fichter, J. et al, "Sleep-Related Breathing Disorders are Associate with Ventricular Arrhythmias in Patients with an Implantable Cardioverter-Defibrillator" *Chest,*vol. 122, pp. 558-561, Aug. 2002.

Garrigue, S. et al "Sleep Apnea: A New Indication for Cardiac Pacing?," *Pace,* vol. 27, pp. 204-211, Feb. 2004.

Glenn W. W. L., "Diaphragm Pacing: Present Status," *PACE,* 1: 357-370, Jul.-Sep. 1978.

Glenn, W., et al. "Diaphragm Pacing" *Journal of Thoracic and Cardiovascular Surgery,* vol. (75):2, pp. 273-281, 1978.

Gosselink, R. "Controlled Breathing and Dyspnea in Patients With Chronic Obstructive Pulmonary Disease," *Journal of Rehabilitaiton Research and Development,* 40(5):20-31, Supplement 2, Sep./Oct. 2003.

Gottlieb, Joshua D., et al., "Hypoxia, Not the Frequency of Sleep Apnea, Induces Acute Hemodynamic Stress in Patients With Chronic Heart Failure", JACC, vol. 54, No. 18, 1707-1712, 2009.

Harish, A. et al, "Laparoscopic Implant Device for Intramuscular Electrodes," *IEEE-EMBC and CMBCC,* pp. 1167-1168, 1995.

Hayano, J. et al "Respiratory Sinus Arrhythmia: A Phenomenon Improving Pulmonary Gas Exchange and Circulatory Efficiency," *Circulation,* vol. 94, pp. 842-847, 1996.

Heinzer, R., et al, "Lung Volume and Continuous Positive Airway Pressure Requirements in Obstructive Sleep Apeau" *American Journal of Respiratory and Critical Care Medicine,* vol. 172, pp. 114-117, 2005.

Hennersdorf, M.G. et al, "Chemoreflexsensitivity in Chronic Heart Failure Patients," *European Journal of Heart Failure,* vol. 3, pp. 679-684, 2001.

Iazzo, P. ed., "Handbook of Cardiac Anatomy, Physiology, and Devices", p. 398, 2009.

Ishii, K. et al "Effects of Bilateral Transvenous Diaphragm Pacing on Hemodynamic Function in Patients after Cardiac Operations," *J Thorac Cardiovasc Surg,* vol. 100, pp. 108-114, 1990.

Javaheri, S. et al, "Sleep Apnea in 81 Ambulatory Male Patients with Stable Heart Failure: Types and Their Prevalences, Consequences, and Presentations," *Circulation,* vol. 97, pp. 2154-2159, 1998.

Jensen, A. et al., "Signal Transduction in Smooth Muscle,: Airway caliber in healthy and asthmatic subjects effects of bronchial challenge and deep inspirations," *J. Appl Physiol,* 91:506-515, 2001.

Kaszala Karoly et al., "Sensors and Algorithms for Pacemakers and Implantable Cardioverter Defibrillators", Ciculation 122:1328-1340, 2010.

Kohnlein, T. et al, "Central Sleep Apnea Syndrome in Patients with Chronic Heart Disease: a Critical Review of the Current Literature," *Thorax,* vol. 57, pp. 547-554, 2002.

Koyner, JL et al., Mechanical Ventilation and the Kidney. Blood Purification. 19 Nov. 1-22, 2009. vol. 29; DOI: 1 0.1159/ 000259585; pp. 52-68; p. 55, paragraphs 2-3.

Krachman, S. et al "Comparison of Oxygen Therapy with Nasal Continuous Positive Airway Pressure on Cheyne-Stokes Respiration During Sleep in Congestive Heart Failure," *Chest,* vol. 116, pp. 1550-1557, Dec. 1999.

LaFond, C. et al "Impact of CPAP on Asthmatic Patients with Obstructive Sleep Apnoea," *Eur Respir J,* vol. 29, pp. 307-311, 2007.

(56) References Cited

OTHER PUBLICATIONS

Lanfranchi, P.A. et al, "Prognostic Value of Nocturnal Cheyne-Stokes Respiration in Chronic Heart Failure," Circulation, pp. 1435-1440, 1999.
Lau, Chu-Pak et al., "Optimizing heart failure therapy with implantable sensors", Journal of Arrhythmia, 28:4-18, 2012.
Leung, R. et al, "Sleep Apnea and Cardiovascular Disease," Am J Respir Crit Care Med, vol. 164, pp. 2147-2165, 2001.
Liem, L.B., "EP 101: Ventricular Tachycardia", EP Lab Digest, v.7, No. 8, Aug. 2007.
Malkin R. et al., "The Effect of inducing Ventricular Fibrillation with 50-Hz Pacing Versus T are Stimulation on the Ability to Defibrillate", Pacing and Clinical Electrophysiology, vol. 21 issue 5: May 1998.
Mathew. O., "Effects of Transient Intrathoracic Pressure Changes (hiccups) on Systemic Arterial Pressure," J Appl Physiol, vol. 83, pp. 371-375, 1997.
Merchant, Faisal M. et al., "Implantable Sensors for Heart Failure", Circ Arrhythm Electrophysiol.; 3:657-667, 2010.
Mitsuyana. T. et al, "Diaphragm Pacing With the Spinal Cord Stimulator," Aeta Neurochir, 87:89-92, 2003.
Norton, J., "Toward Consistent Definitions for Preload and Afterload," Advan in Physiol Edu, vol. 25, pp. 53-61, Mar. 2001.
Noshiro, M. et al., "Method of Electrophrenic Respiration for Producing a Natural Respiratory Flow Rate Using Feedback Control of Tidal Volume Waveform," Med. & Bio. Eng. & Comput., 20:765-71, Nov. 1982.
Patroniti, M.D., et al "Sigh improves Gas Exchange and Lung Volume in Patients with Acute Respiratory Distress Syndrome Undergoing Pressure Support Ventilation," Anesthesiology,96:788-794, 2002.
Peters, J. et al, "Negative Intrathoracic Pressure Decreases Independently Left Ventricular Filling and Emptying;" American Physiological Society, pp. H120-H131, 1989.
Pinsky, M. "Cardiovascular Issues in Respiratory Care," Chest, vol. 128, pp. 592-597, Nov. 2005.
Reeve, C., "New Implantable Breathing Device," University Hospitals of Cleveland, pp. 1-4, 2003.
Reeve, C., Christopher Reeve Paralysis Foundation Questions & Answers, pp. 1-3, Mar. 13, 2003.
Sauermann, S. et al, "Computer Aided Adjustment of the Phrenic Pacemaker: Automatic Functions. Documentation, and Quality Control," Artificial Organs, 21(3):216-217, 1997.
Schmit, B. D. et al, "Laparoscopic Placement of Electrodes for Diaphragm Pacing Using Stimulation to Locate the Phrenic Nerve Motor Points," Transactions on Rehabilitation Engineering, 6(4):382-390, Dec. 1998.
Schultz, R. et al "Nocturnal Periodic Breathing in Primary Pulmonary Hypertension," Eur Respir J, vol. 19, pp. 658-663, 2002.
Series, F. et al, "Assessment of Upper Airway Stabilizing Forces with the Use of Phrenic Nerve Stimulation in Conscious Humans," J Appl Physiol, vol. 94, pp. 2289-2295, 2003.
Series, F. et al, "Increasing the Functional Residual Capacity May Reverse Obstructive Sleep Apnea Sleep," 11(4):349-353, 1988.
Shaul, D.B. et al, "Thoracoscopic Placement of Phrenic Nerve Electrodes for Diaphragmatic Pacing in Children," Journal of Pediatric Surgery, 37:974-978, Jul. 2002.
Shier, D. et al, Hole's Human Anatomy & Physiology,pp. 798 (2 pages total), Jan. 6, 2009.
Simon, P. et al, "Vagal Feedback in the Entrainment of Respiration to Mechanical Ventilation in Sleeping Humans," J. App. Physiol. 89:760-769, 2000.
Sin, D. "Effects of Continuous Positive Airway Pressure on Cardiovascular Outcomes in Heart Failure Patients With and Without Cheyne-Stokes Respiration" Circulation, 102:61-66, Jul. 4, 2000.
Sorli, J. et al., "Ventilatory Assist Using Electrical Stimulation of AJdominal Muscles," IEEE Transactions of Rehabilitation Engineering, vol. 4, No. 1, pp. 1-6, Mar. 1996.
Taira, T. et al, "Phrenic Nerve Stimulation For Diaphragm Pacing With a Spinal Cord Stmulator," Surg Neurol. 59:128-132, 2003.
Van Houwelingen, K. et al "The Sleep Apnoea Syndromes," European Heart Journal, vol. 20, pp. 858-866, Jun. 1999.
VIASYS Healthcare, "Ventilation Requires Perfect Balance", SensorMedics® 3100A HFOV, VIASYS Healthcare Brochure, 2 pages.
Wolk R. et al "Sleep-Disordered Breathing and Cardiovascular Disease," Circulation, vol. 108, pp. 9-12, Jul. 2003.
Yim S. et al "Contnuous Positive Airway Pressure for Asthma: Not a Big Stretch?," Eur Respir J, vol. 29, pp. 226-228, 2007.

* cited by examiner

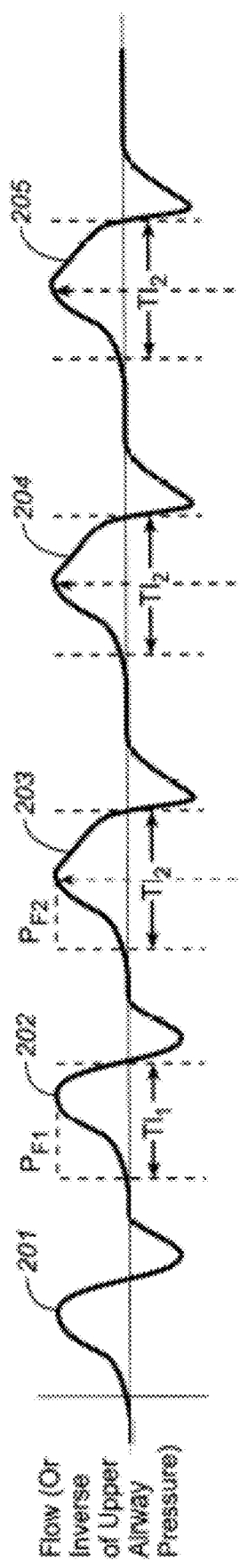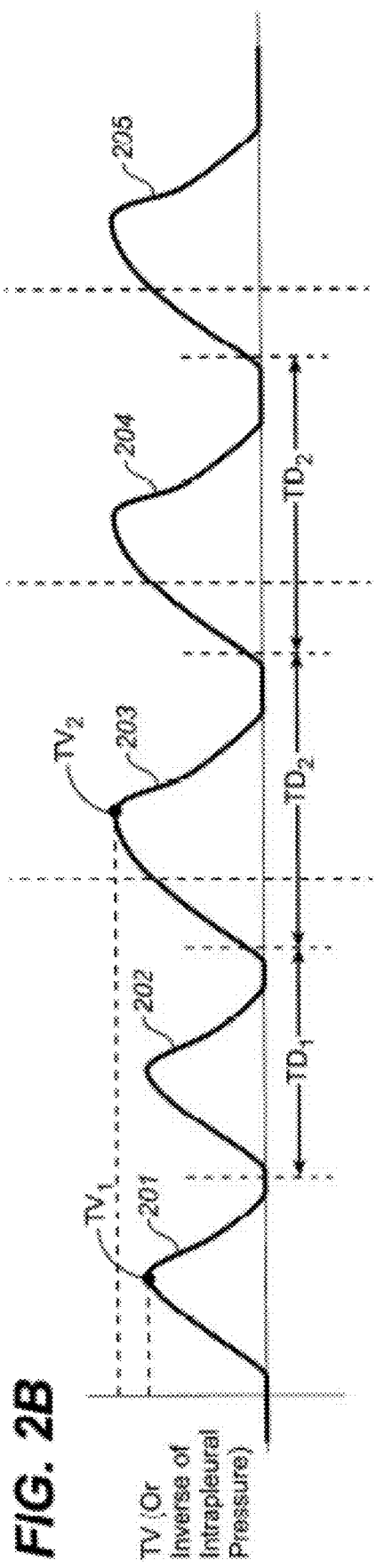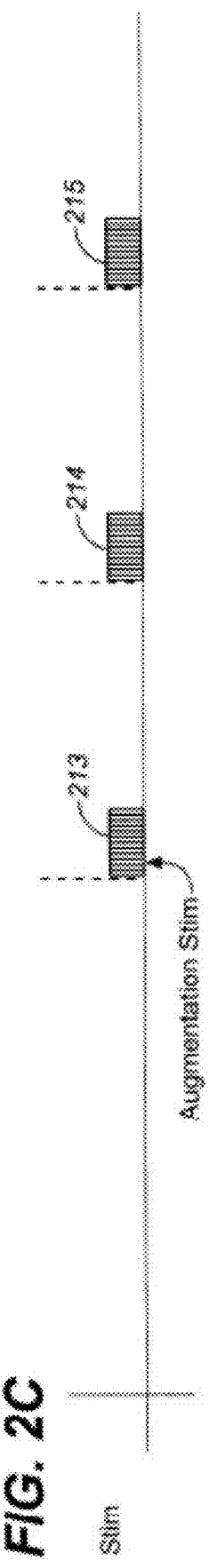

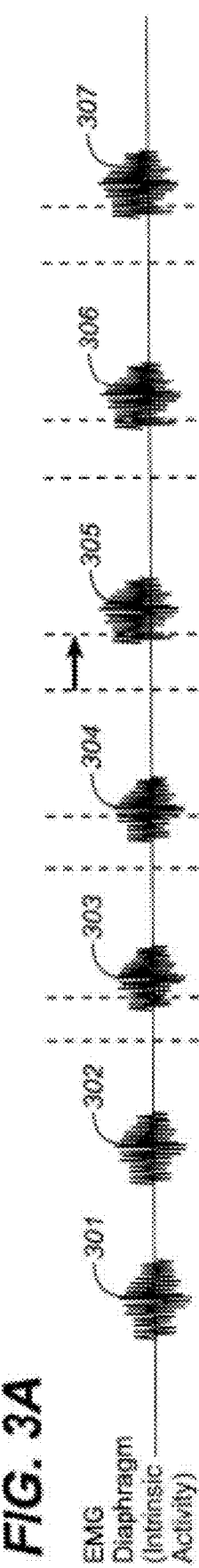
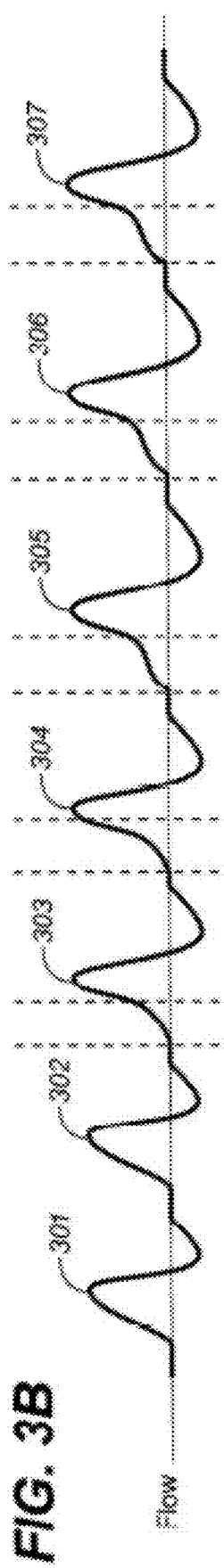
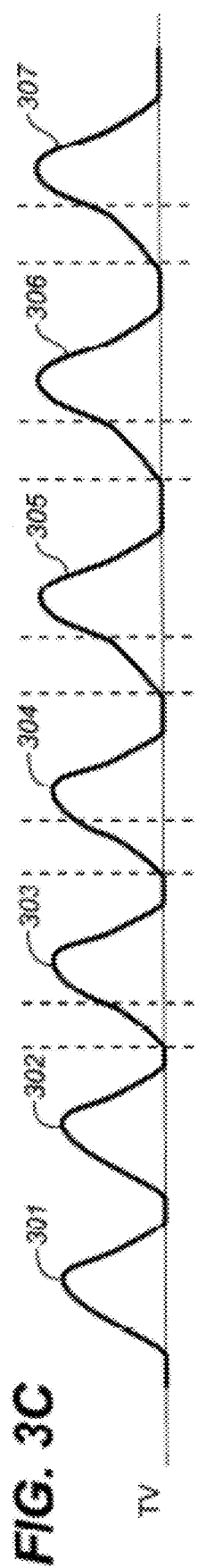
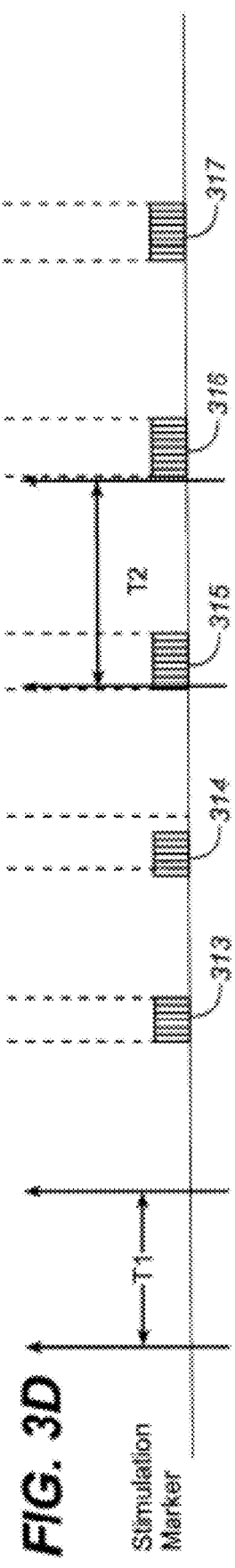

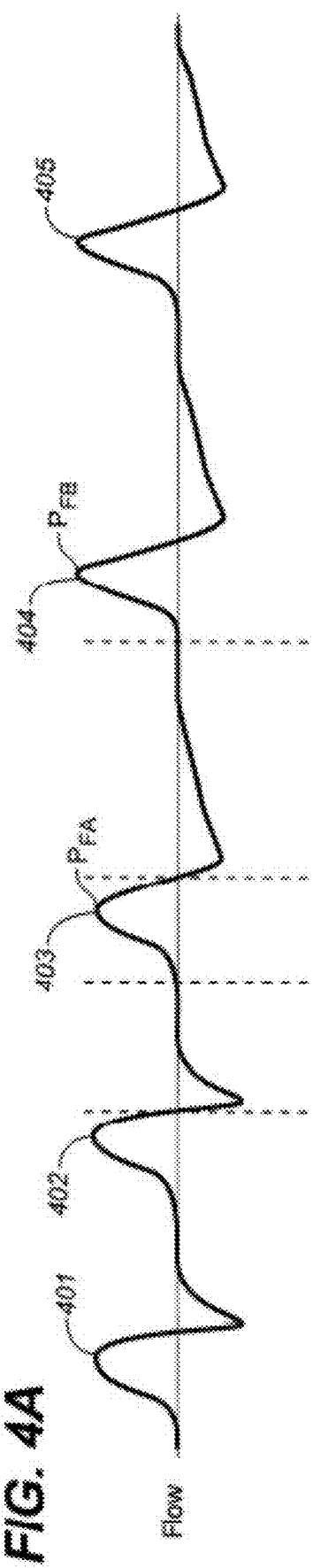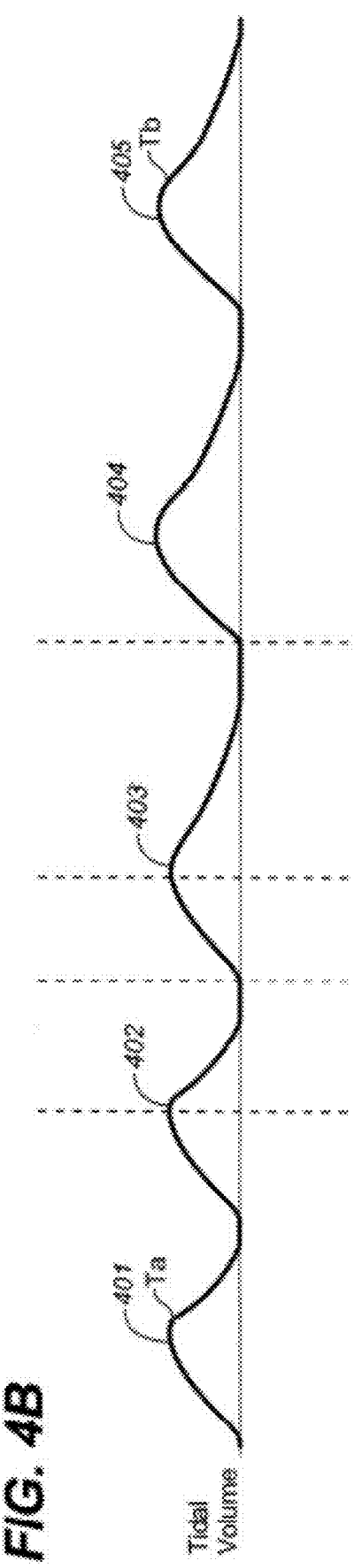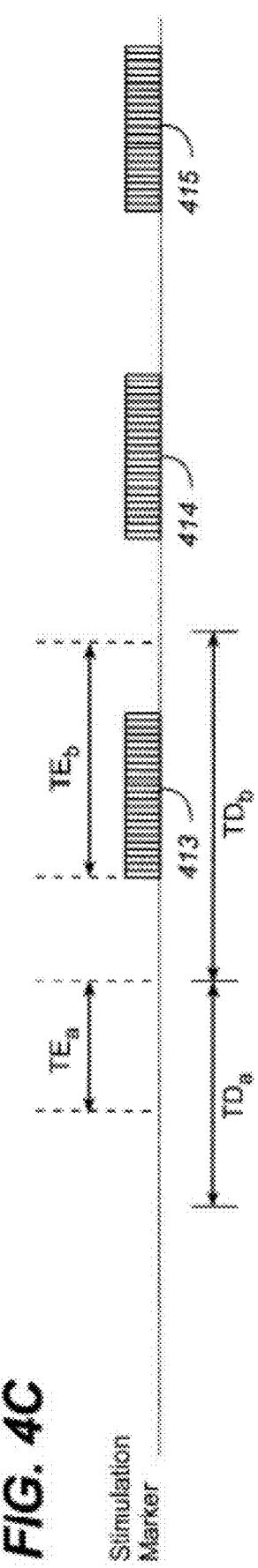

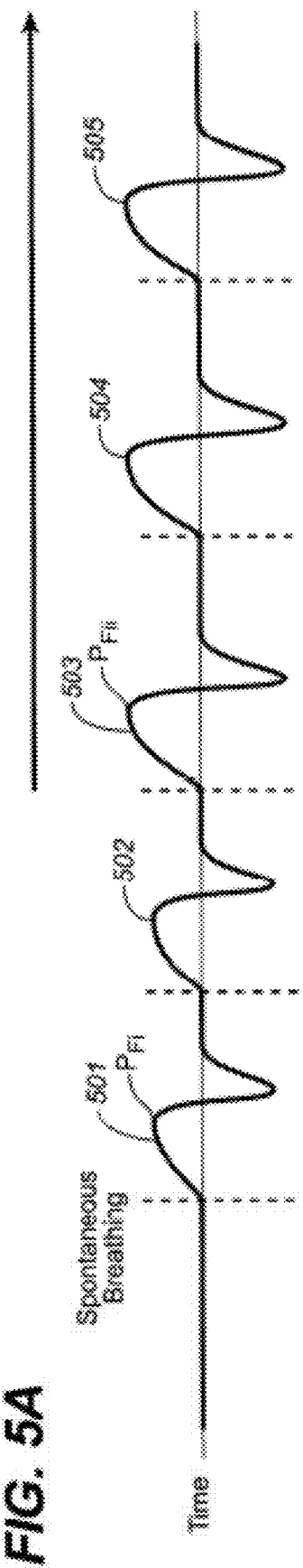
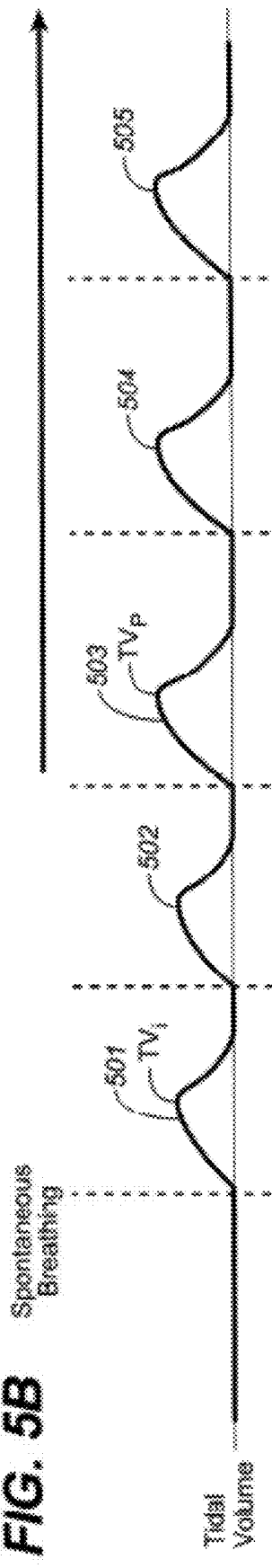
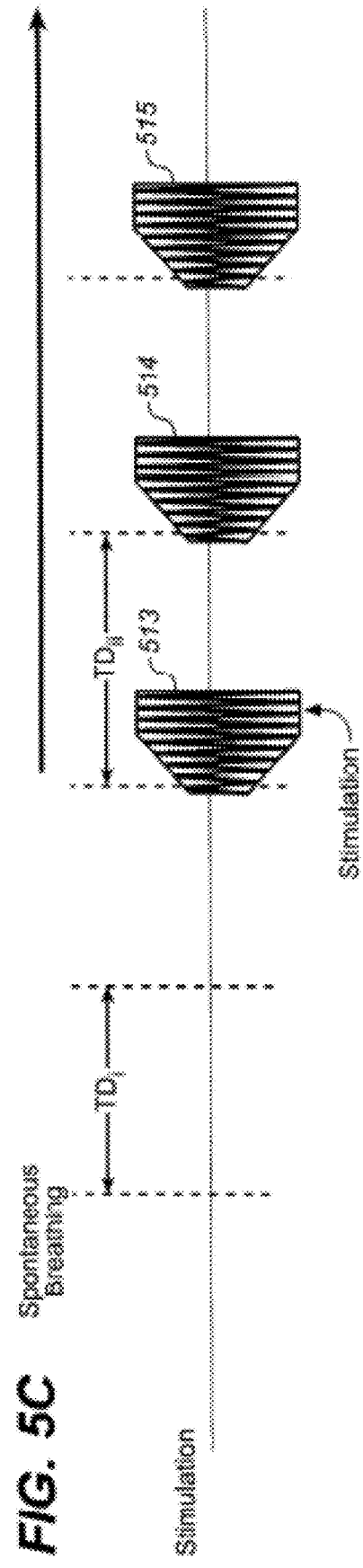
FIG. 5A
FIG. 5B
FIG. 5C

DEVICES AND METHODS FOR REDUCING INTRATHORACIC PRESSURE

CROSS-REFERENCE TO RELATED APPLICATIONS

This application is a continuation of International Application No. PCT/US2015/047042 filed Aug. 26, 2015 which claims the benefit of priority to U.S. Provisional Application No. 62/041,987 filed Aug. 26, 2014, the contents of which are incorporated herein by reference in their entirety.

FIELD OF THE INVENTION

The present invention relates to treating heart failure (or dysfunction) and other cardiovascular disorders. In particular, the present invention relates to treating heart failure using one or more implantable or non-implantable sensors along with phrenic nerve stimulation to reduce intrathoracic pressure and thereby reduce pulmonary artery, atrial, renal, and ventricular pressures leading to reduced complications and hospitalization. The present invention targets treating acute decompensated heart failure (ADHF) utilizing a temporary or removable catheter or electrode as well as a fully chronic implantable device for long-term treatment of heart failure and pulmonary hypertension patients.

BACKGROUND OF THE INVENTION

Heart failure is a complex disease with many forms and causes. In general heart failure is defined as a condition where the cardiac output is not adequate to meet the metabolic needs of the body, either at rest or with exercise. Heart failure may be preceded by heart dysfunction, including, but not limited to ventricular dysfunction.

There are two forms of heart failure, one where the hearts ability to expel the blood is impaired (systolic heart failure), another where there is a defect in ventricular filling (diastolic heart failure). Each can occur in isolation or together.

Current treatments for heart failure are available to slow the progress of the disease but do not cure the disease. Despite all the current therapeutic options, studies show that more than half of heart failure patients die within 5 years of their diagnosis.

Accordingly it would be desirable to provide new and useful treatments for heart failure or other cardiac/cardiovascular disease.

Pacemakers have been useful where there are cardiac bradyarrhythmias. Defibrillators are primarily used to prevent sudden cardiac death and therefore have not improved the status of heart failure patients nor have they improved quality of life. Cardiac Resynchronization Therapy devices (CRTs) have been useful or in patients with significant interventricular delay or in preventing cardiac tachyarrhythmias or sudden cardiac death (CRT-Ds). There are many heart failure patients who may not substantially benefit from one or more of these treatments or may not have an improved quality of life from such treatments. For example, CRTs have not been approved for patients with ejections fractions greater than 35% and thus are not available for diastolic heart failure patients who typically have ejection fractions greater than 50%, or for systolic patients with an ejection fraction greater than 35%. Some studies show diastolic heart failure to account for up to ⅓ of the patients presenting with heart failure. In addition, because the current treatments do not cure heart failure, additional treatment that may be used in combination with existing treatment may be beneficial to the patients. Other devices such as temporary or chronic implants stimulate the vagal nerve or cardiac plexus nerves to reduce the heart rate and/or improve cardiac contractility and achieve improved cardiac output.

Many of the drugs such as calcium channel blockers, beta blockers, ACE inhibitors, diuretics, nitrates have had varying degrees of effect on different manifestations of heart failure. However, not all are useful to treat all heart failure patients. Furthermore, due to side effects some patients withdraw from treatment. Pharmacological therapeutic approaches to diastolic heart failure currently recommend diuretics and nitrates while the efficacy is uncertain for all diastolic heart failure patients with calcium channel blockers, beta blockers, ACE inhibitors. Inotropic agents are not recommended for diastolic patients. Accordingly it would be desirable to provide treatment for heart failure that may be used alone or in combination with other heart failure treatments. It would also be desirable to provide alternative or supplementary treatment for diastolic heart failure patients.

Another cardiovascular condition that may exist with or without heart failure is hypertension. Hypertension is believed to worsen heart failure. It is also believed that hypertension may lead to diastolic heart failure. Studies have shown that treatment of hypertension reduces the incidence of heart failure by 30% to 50%. Accordingly it would be desirable to provide a treatment for hypertension.

In addition, a large percentage of heart failure patients also suffer from one or more forms of sleep apnea; obstructive sleep apnea or central sleep apnea, (each of which have significant clinical differences), or mixed apneas. These conditions are believed to worsen progression of heart failure. Obstructive sleep apnea is also believed to contribute to the development of heart failure, particularly through hypertension.

Oxygen desaturations at night, changes in intrathoracic pressure, and arousals may adversely affect cardiac function and eventually result in an imbalance between myocardial oxygen delivery and consumption. In heart failure patients with sleep apnea, there is believed to be an increased incidence of atrial fibrillation, ventricular arrhythmias and low left ventricular ejection fraction. Atrial fibrillation may be caused in part by increased right heart afterload due to hypoxic vasoconstriction which produces pulmonary hypertension. Periodic breathing such as Cheyne-Stokes associated with CSA, create wide fluctuations in intrathoracic pressure with a negative cardiovascular impact. Central sleep apnea sometimes goes undiagnosed in heart failure patients. The untreated central sleep apnea may trigger a negative chain of events that leads to worsening of heart failure.

Obstructive sleep apnea is believed to elicit a series of mechanical, hemodynamic, chemical, neural and inflammatory responses with adverse consequences for the cardiovascular system for example, as described in *Sleep Apnea and Heart Failure Part I: Obstructive Sleep Apnea. Bradley, Douglas T, MD, Floras, John S., MD D Phil, Circulation Apr.* 1, 2003. Many of these effects are believed to exacerbate conditions of heart failure. Among these responses, increases in blood pressure as well as increases in sympathetic activity are associated with obstructive apneas. Obstructive sleep apnea also causes significant changes in intrathoracic pressure during apneic episodes applying further pressure on the heart.

Accordingly it would be desirable to treat sleep apnea in heart failure to reduce the negative effects of the apnea on the patient's disease status.

CPAP is the most common treatment for obstructive sleep apnea and has been proposed for central sleep apnea. CPAP requires an external device and patient compliance. In addition, its cardiovascular effects are currently unclear and some researchers believe that it can exacerbate heart failure in some patients, particularly where positive forced pressure has a negative effect on a heart failure patient, such as, for example, in patients where a reduced ventricular filling would significantly reduce cardiac output. Diaphragm stimulation has been proposed to treat central sleep apnea by stimulating when apnea has occurred. However, the stimulation is provided after the apnea event has occurred rather than preventing the apnea event. Hypoglossal nerve stimulation has been proposed to treat obstructive sleep apnea by increasing patency in the upper airway to allow respiration.

It would accordingly be desirable to provide a treatment for sleep apnea that has a symbiotic therapeutic effect in treating heart failure or other cardiac/cardiovascular disease.

It would further be desirable to provide a treatment for heart failure patients with sleep apnea that provides a separate or additional function of treating heart failure.

Research has shown that voluntary control of breathing can improve cardiac disease, including hypertension and heart failure. It is believed that the reason for this is a biofeedback that exists between the cardiac and respiratory systems due to baroreceptor based reflexes, and also a common central nervous control. Biofeedback systems for breathing control have been provided. However, they require patient compliance and diligence. Furthermore, because they require patient compliance, the therapy can only occur during waking hours.

Heart failure is a chronic condition which leads to a reduction in cardiac output and an increase in pulmonary pressures which in turn leads to pulmonary congestion and hospitalization. Yet various studies have shown significant increases in stroke volume and cardiac output, particularly in patients who have undergone a CABG procedure, when negative extrathoracic pressure is reduced. For example, results may be seen in further detail in the following:

Parker, J. et al, "Reducing Cardiac Filling Pressure Lowers Norepinephrine Spillover in Patients With Chronic Heart Failure", Circulation, 2000; 101:2053-2059.

CHATURVEDI, R. et al., "Use of Negative Extrathoracic Pressure to Improve Hemodynamics After Cardiac Surgery", *The Annals of Thoracic Surgery*, 2008; 85, pp. 1355-1360, 2008.

GOTTLIEB, J. et al., "Hypoxia, Not the Frequency of Sleep Apnea, Induces Acute Hemodynamic Stress in Patients With Chronic Heart Failure", *Journal of the American College of Cardiology*, Vol. 54, No. 18, pp. 1706-1712, Oct. 27, 2009.

MERCHANT, F. et al., "Implantable Sensors for Heart Failure", *Circulation: Arrhythmia and Electrophysiology*, 2010; 3, pp. 657-667, 2010.

BOCCHIARDO, M. et al., "Intracardiac impedance monitors stroke volume in resynchronization therapy patients", *Europace: Journal of the European Heart Rhythm Association*, (2010) 12, pp. 702-707, Feb. 25, 2010.

KASZALA, K. et al., "Device Sensing: Sensors and Algorithms for Pacemakers and Implantable Cardioverter Defibrillators", *Circulation, Journal of the American Heart Association*, 2010; 122, pp. 1328-1340, Sep. 28, 2010.

LAU, C. et al., "Optimizing heart failure therapy with implantable sensors", *Journal of Arrhythmia*, 28(2012), pp. 4-18, Mar. 9, 2012.

Each of these references is incorporated herein by reference in its entirety and for any purpose.

Previous attempts have been made to utilize an implantable medical device to stimulate a patient's diaphragm to affect cardiac output. For instance, U.S. Pat. No. 7,277,757 to Casavant et al. discloses an implantable medical device that stimulates a nerve, such as a phrenic nerve, associated with respiration to cause a diaphragm of a patient to contract. The implantable medical device receives a signal (e.g., detecting a ventricular tachyarrhythmia, sensing a pressure that indicates a need for increased cardiac output, or receiving a signal from a patient via a patient activator) that indicates a need for increased cardiac output and stimulates the nerve in response to the signal. Stimulation of the nerve may increase cardiac output of a beating or defibrillating heart.

However, Casavant et al. fails to disclose pressure sensing and creating lung volume with a reduction in intrathoracic pressure. Moreover, Casavant synchronizes its stimulation to the pacing of the heart and increases the amplitude of at least some of the pacing pulses rather than providing for a sustainable stimulation over a continuous period of time.

SUMMARY OF THE INVENTION

In accordance with the invention, stimulation is provided to the diaphragm or phrenic nerve to elicit a diaphragm response to thereby provide a therapeutic effect for a heart failure or other cardiac or cardiovascular patient.

In accordance with one aspect of the invention, stimulation to elicit a diaphragm response is provided to increase or normalize lung volume and in particular to increase functional residual capacity. It is believed that stimulation to increase or to normalize lung volume or functional residual capacity may have one or more effects that may be therapeutic to cardiovascular or heart failure patients. Normalizing herein may include for example, bringing a physiological parameter into a normal or healthy region for patients or for a particular patient, or to a level appropriate for a condition or state of a patient.

In accordance with another aspect of the invention stimulation is provided to control breathing to reduce respiration rate and thereby reduce hypertension, reduce sympathetic nerve bias, and/or provide improved blood gas levels.

In accordance with another aspect of the invention stimulation is provided to control minute ventilation to therapeutically effect blood gas levels.

In accordance with another aspect of the invention, stimulation is provided to create a deep inspiration or an increased tidal volume to thereby reduce sympathetic nerve bias, improve blood gas levels, stimulate reflexes for example the Hering-Bruer reflex related to activating stretch receptors, increase lung volume, normalize or reset breathing or provide other beneficial therapies to improve cardiovascular function or heart failure condition.

In accordance with another aspect of the invention stimulation may be provided to modulate intrathoracic pressure to thereby produce a therapeutic effect. Modulation of intrathoracic pressure is expected to impact sympathetic activation and improve heart conditions. It is known that in chronic heart failure settings, increased cardiac filling pressures and/or pulmonary pressures may cause a direct or indirect reflex increase in sympathetic efferent outflow to the heart. Therefore, a sustained reduction or average reduction in intrathoracic pressure through modulation of intrathoracic pressure could have an opposite effect and reduce sympathetic efferent outflow to the heart. One would expect to reduce norepinephrine spillover through intrathoracic pressure modulation which is beneficial to the heart failure patient. Parker et al. used a lower body pressure chamber to show certain reduction in body pressure leads to reduction in cardiac filling pressures leading to reduction in norepinephrine spillover in acute setting. Longer term application this therapy has potential to improve the heart failure and also remodel the cardiac tissue.

The devices and methods described may achieve similar results through various modes of phrenic nerve and/or diaphragm stimulation. These stimulation modalities include low-level stimulation overlapped with patient intrinsic breathing, diaphragm bias, breath augmentation, increase in tidal volume, increase in inspiration duration, deep inspiration, breathing entrainment, manipulation of exhalation period and volume, increasing and maintain resting lung volume or functional residual capacity, sustained stimulation during inspiration and/or exhalation, continuous stimulation, stimulation synchronized with respiratory cycles, or cardiac cycles, and/or duty-cycled type stimulation based on a percentage of time, for example, 20% of the time during the day or night and when patient is sleep or awake. The duty-cycled type stimulation could be synchronized to a respiratory cycle or not.

In accordance with another aspect of the invention, stimulation may be provided to modulate intrathoracic pressure targeting a sustained reduction in average central venous pressure to effectively reduce right arterial and right ventricular pressures and pulmonary wedge pressure. Reduction in right ventricular pressure in heart failure patients leads to increase stroke volume and therefore cardiac output. The sustained increase in cardiac output though reduction in filling pressure will lead to reductions in pulmonary congestion which is a major reason for acute heart failure decompensation and therefore hospitalization. Some other hemodynamic effects of this stimulation could be reduction in heart rate as results of increased in cardiac output and/or reduction in filling pressures.

In accordance with another aspect of the invention, stimulation may be provided to modulate intrathoracic pressure targeting a sustained or incremental reduction in renal pressure or the average renal pressure to improve kidney function and filtration. Abnormal renal function is common in acute and chronic heart failure. It is expected a change in blood volume, cardiac filling pressures, central venous pressure, atrial or ventricular pressures, cardiac output, and/or hemodynamics intervention could lead to improvement of renal function. Intrathoracic pressure modulation could have an impact on pressure within inferior and superior vena cava as well as central venous pressures. Activation of renal sympathetic activity through modulation and manipulation of these pressures could have an impact on kidney pressure and blood transfer rate and ultimately kidney glomerular filtration rate (GFR) and leading to reduction in kidney failure as well as reducing congestion or blood backing up into the lungs through increased filtration. Any of the mentioned phrenic nerve or diaphragm stimulation modalities included in this application could be applied at various situations depending on the need of the patient and sensed parameters. Literature has shown that elevated cardiac filling pressures are associated with reduced GFR. Therefore the present invention tries to reduce cardiac filling pressure through phrenic nerve stimulation and to increase GFR.

In accordance with another aspect of the invention, intrathoracic pressure modulation could be used to treat patients with pulmonary hypertension. Pulmonary hypertension is result of increased pulmonary pressures. Reduction or modulation of intrathoracic pressure could lead to reduction or treatment of pulmonary hypertension.

In accordance with another aspect of the invention the stimulation could be activated by the patient using an external device. The stimulation could be also activated by sensing increased physical activity through an activity sensor or increased in heart rate or respiration rate or other mechanism indicating need for supplemental cardiac output or reduction in filling pressures. For example, a thoracic or lungs impedance sensor or a list of sensors including in the referenced publication cold be used to activate stimulation to deliver therapy to improve hemodynamics.

In accordance with another aspect of the invention stimulation is provided to reduce breathing disorders to thereby improve condition of a heart failure patient.

In accordance with another aspect of the invention a combined cardiac rhythm management device including leadless devices and diaphragm/phrenic nerve stimulation device is provided to provide an enhanced combined treatment device.

In accordance with another aspect of the invention, leadless phrenic nerve electrodes could be injected, delivered, or placed in the vicinity of the phrenic nerve and stimulation cold be performed through an external or integral pulse generator. The sensor or sensors to synchronize the stimulation could be also internal or external to the body.

In accordance with another aspect of the invention a combined vagal nerve, hypoglossal nerve, or cardiac plexus stimulation management device and diaphragm/phrenic nerve stimulation device is provided to provide an enhanced combined treatment device.

The system may also be utilized to provide a continuous or synchronized low level stimulation to the phrenic nerve or diaphragm overlapped with the patient's own intrinsic breathing to reduce an intrathoracic pressure and improve cardiac output. The patient's SaO2 levels may also be improved and the heart and respiration rates may be reduced.

Various mapping and/or neurostimulating electrodes may be utilized with the methods and devices described herein. For instance, such mapping and/or neurostimulating electrodes may be employed in conjunction with a cardiac pacemaking or defibrillation lead and more particularly a mapping and neurostimulation electrodes employed over the cardiac pacemaking or defibrillation lead while the cardiac lead is either in vivo and resident within the vascular structure. These electrodes may be placed simultaneously with neurostimulation electrodes or leads. The mapping and neurostimulation electrodes used in conjunction with the cardiac pacemaking or defibrillation lead herein is referred to as the mapping and neurostimulation electrodes.

The mapping and neurostimulation electrodes may be employed in conjunction with a cardiac lead and for interventional therapy such as neurostimulation to patients who have already had a cardiac lead installed.

Such electrodes also overcome many of the problems that exist with conventional cardiac leads or cardiac leads with integral neurostimulation electrodes. If a patient has been implanted with an existing, conventional cardiac lead and that same patient requires additional interventional neurostimulation at any point after the existing cardiac lead has been implanted, the original cardiac lead must be explanted and the entire cardiac lead must be replaced. The electrodes described herein may be installed over the excising cardiac lead and advanced down the cardiac lead body into a therapeutic position without removing or re-positioning the existing cardiac lead.

In addition, a conventional cardiac lead with integral neurostimulation electrodes, whether the neurostimulation electrodes are integral to the cardiac lead or whether the neurostimulation electrodes are sutured onto the cardiac lead, typically must be installed concurrently when the cardiac lead is originally installed into the patient. The relationship between the neurostimulation electrode and the cardiac electrode is fixed prior to implant and therefore positioning for either the neurostimulation electrodes or the cardiac electrode is sub-optimal.

Yet the electrodes described herein are completely independent and mobile and have the ability to be installed over an existing cardiac lead. Moreover, the mapping and neurostimulation electrodes can be positioned independently of the cardiac electrodes. This independent positioning ability allows for both mapping and neuro-stimulating electrodes as well as the cardiac electrode's positioning to be optimized.

The temporary or chronic mapping and neurostimulation electrodes could be inserted through several approaches including femoral, radial, right or left Subclavien veins or right or left jugular veins or in other transvenous approaches placed in veins or arteries overlapping right or left phrenic nerve. Some electrode systems/catheters could map and stimulate both phrenic nerves through transvenous approaches. In cases where there are needs for both phrenic nerves to be stimulated simultaneously, with delays, or in sequence, a single electrode/leads system or two electrode/leads systems could be deployed.

Lastly, a conventional cardiac lead with integral neurostimulation electrodes or neurostimulation electrodes sutured onto the cardiac lead body are iso-diametric and are aligned randomly. The random alignment could limit therapy because the electrical field if not focused towards the neural anatomy as the electrodes will not energize the nerve. The electrodes described herein are designed to deploy the neurostimulation electrodes and bias the neurostimulation electrode towards the vessel wall and in a position that is tangent to the neural anatomy residing outside the vessel wall. The biased or focused neurostimulation electrodes assure the electrical field induced by the neurostimulation electrodes is optimized towards the neural anatomy.

These and other aspects of the invention are set forth herein in the abstract, specification and claims.

BRIEF DESCRIPTION OF THE DRAWINGS

FIGS. 2A, 2B and 2C illustrate respectively, flow, tidal volume and stimulation envelope signals corresponding to use of a device and method in accordance with an aspect of the invention.

FIGS. 3A, 3B, 3C and 3D illustrate respectively, EMG, flow, tidal volume and stimulation envelope signals corresponding to use of a device and method in accordance with an aspect of the invention.

FIGS. 4A, 4B, and 4C illustrate respectively, flow, tidal volume and stimulation envelope signals corresponding to use of a device and method in accordance with an aspect of the invention.

FIGS. 5A, 5B, and 5C illustrate respectively, flow, tidal volume and stimulation envelope signals corresponding to use of a device and method in accordance with an aspect of the invention.

DETAILED DESCRIPTION OF THE INVENTION

In accordance with one aspect of the invention, stimulation to elicit a diaphragm response is provided to increase or normalize lung volume and in particular to increase functional residual capacity. It is believed that stimulation to increase or to normalize lung volume or functional residual capacity may have one or more effects that may be therapeutic to cardiovascular or heart failure patients.

In accordance with this aspect of the invention stimulation may be provided using a device or method as described in one or more of the related patent applications set forth herein, to increase or normalize lung volume or functional residual capacity. For example, a bias stimulation may be provided to increase functional residual capacity or to bias lung volume for a period of time. It is believed that increasing functional residual capacity may have one or more therapeutic effects for heart failure or other cardiovascular patients, such as, for example, reducing effort required to breathe; improving gas exchange, improving SaO2 levels; providing a buffer to reduce fluctuations in blood gas levels and to reduce the likelihood of crossing the PCO2 apneic threshold; and reducing episodes of obstructive apnea in OSA patients and central sleep apnea episodes. Such buffer may also stabilize blood gases to counter fluctuations in gas levels caused by circulatory delay that may lead to Cheyne-Stokes respiration and Central Sleep Apnea. Other stimulation may be provided to achieve improved SaO2 levels or gas levels, for example, as set forth in the related patent applications which are incorporated completely and without limitation herein by reference. Other stimulation may be provided that may have the effect of normalizing lung volume, including but not limited to low frequency stimulation, low energy stimulation, or deep inspiration stimulation. These various stimulation techniques may also be provided or configured to have the effect of increasing SaO2 levels to reduce load on the heart and cardiac filling pressures.

Figure 1A:
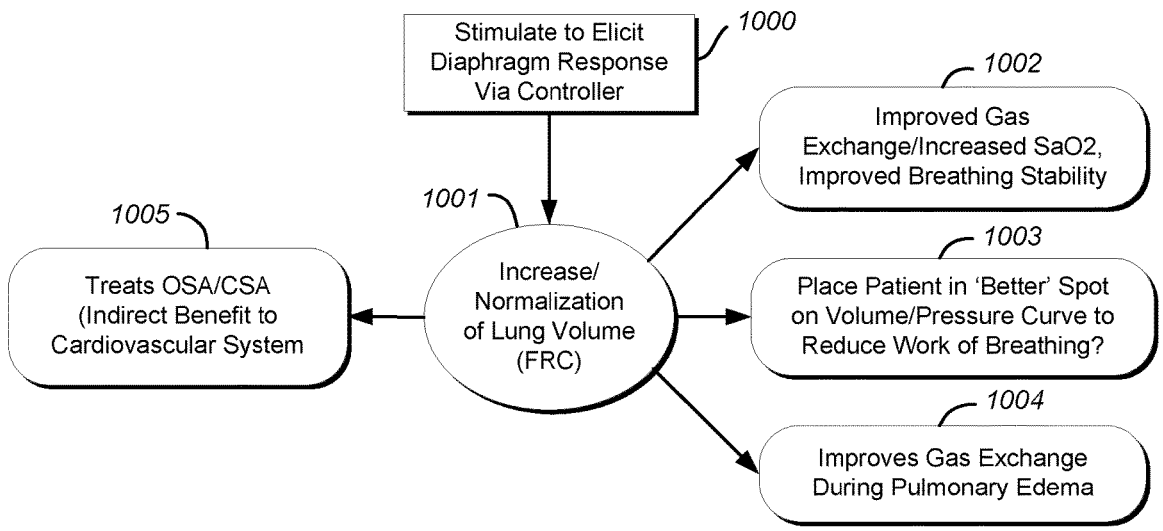
FIG. 1A is a chart illustrating examples of possible beneficial effects of stimulation in accordance with an aspect of the invention.

FIG. 1A illustrates stimulation provided with a device or method in accordance with the invention. Stimulation is provided using a device or method for stimulating tissue to elicit a diaphragm response 1000. Stimulation increases or normalizes lung volume or FRC 1001. The increase or normalization or lung volume may improve gas exchange; increase SaO2, and/or improve breathing stability 1002. The increase or normalization of lung volume or FRC may move a patient to a more optimal location on the volume pressure curve 1003 as described in more detail with respect to FIG. 1B. Providing stimulation to increase FRC may also allow improved gas exchange during pulmonary edema where lung inflation creates a gradient for liquid movement from alveolar space to the extra-interstitium 1004. It is believed that moving fluids to the interstitial space will improve ventilation because removal of fluids from the alveolar region will permit improved gas exchange. An increase or normalization of lung volume or FRC may also treat OSA or CSA in patients with OSA (obstructive sleep apnea) or CSA (central sleep apnea) and thereby benefit the cardiovascular system 1005. For example, one or more devices and methods described in copending patent applications set forth above may be used to treat OSA or CSA. Increased or normalized lung volume, FRC, increased inspiration duration or elongated exhalation period all lead to reduction in average, sustained, or instantaneous intrathoracic pressures leading to improved cardiac, pulmonary, and renal pressures all simultaneously lead to reduction or prevention of pulmonary congestion.

Figure 1B:
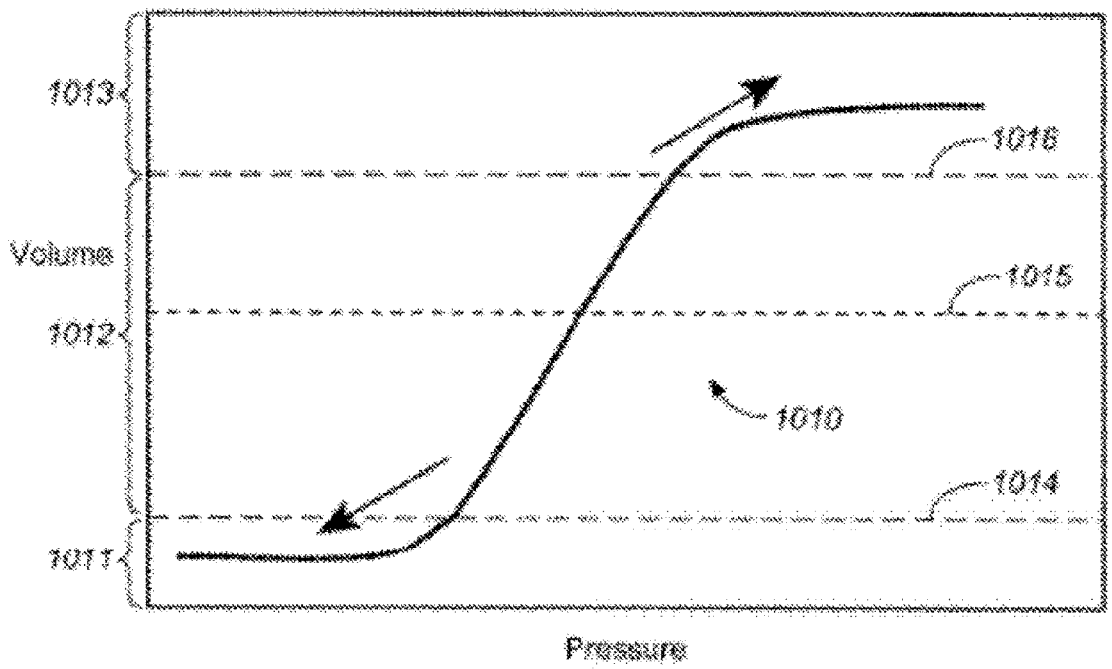
FIG. 1B is a pressure volume curve illustrating use of stimulation in accordance with an aspect of the invention.

FIG. 1B illustrates a pressure/volume curve 1010 illustrating a relationship between transthoracic pressure and lung volume. This example illustrates, among other things how stimulation may be provided to reduce breathing effort and/or intrathoracic pressure change for a given inspiration volume. At lower lung volumes 1011, a greater change in pressure is required to increase lung volume a given amount through inspiration, thus providing a greater work of breathing and thereby increasing metabolic requirements and load on heart as well. Similarly at higher lung volumes 1013, greater change in pressure and effort are required to increase lung volume through inspiration. However, in between the lower volumes 1011 and higher volumes 1013 there is a steeper portion of the curve 1012 where at a given lung volume, inspiration produces an efficient increase in lung volume with less change in pressure required to effect a given volume and therefore less effort required by the respiratory muscles to produce a given change in pressure. It is believed that an increase in required effort to breathe may result in poorer breathing or less effort and gas exchange, particularly in heart failure patients. It is also believed that greater fluctuations in intrathoracic pressure may contribute the conditions affecting heart failure. Thus in accordance with one aspect of the invention, stimulation may be provided to increase resting lung volume so that greater breathing efficiency and gas exchange is provided. Where a patient's normal resting lung volume or functional residual capacity is typically low, it may be increased. Where a patient's resting lung volume is lower than normal for a healthy individual, it may be normalized so that it is brought to a level where efficient breathing occurs. For example a low lung volume 1014 may be increased to higher lung volumes 1015 or 1016 which are at an efficient volume 1012 on the pressure volume curve 1010.

Stimulation may be provided on a sustained or intermittent basis. Stimulation may be provided when a patient is asleep or awake. In accordance with one aspect of the invention, stimulation is provided to compensate for lung volume lost at the onset of sleep or during sleep. In accordance with one aspect of the invention the stimulator may be turned on by the patient prior to sleeping or may be triggered by a sensed parameter or real time clock. A sensor may be used to sense one or more physiological parameters indicating onset or a specific stage of sleep. Other sensors may sense one or more conditions that may be used to determine appropriate times or parameters for stimulation.

In accordance with another aspect of the invention stimulation is provided to control breathing to reduce respiration rate and thereby improve, prevent or slow cardiac disease by reducing hypertension, reducing sympathetic nerve activation, providing SaO2 levels, and/or increasing cardiac output. It is believed that lowering breathing rate will provide a decrease in cardiac rate, and an enhanced vagal response.

In accordance with one aspect of the invention, breathing rate may be controlled by augmenting breathing or stimulating during intrinsic breathing to increase peak tidal volume and/or to increase inspiration duration. Increasing the duration of inspiration or tidal volume it is believed will cause the timing of the next intrinsic breath to be delayed due to the central nervous controller tendency to maintain minute ventilation in absence of any change at the chemoreceptor level. The rate may be continuously slowed by detecting each intrinsic breath and providing stimulation or augmenting until the duration of inspiration, tidal volume or exhalation rate is at a level that brings the breathing rate to a desired rate which is reduced by the central nervous control of minute ventilation.

FIGS. 2A to 2C illustrate stimulation during intrinsic breathing in accordance with one aspect of the invention. FIG. 2A illustrates flow for breaths 201, 202, 203, 204 and 205. FIG. 2B illustrates tidal volume of breaths 201, 202, 203, 204, and 205. Breaths 201, 202 are intrinsic breaths. Breaths 203, 204, and 205 are intrinsic breaths that are augmented by stimulation configured to elicit a diaphragm response as illustrated schematically by stimulation markers 213, 214, and 215.

Stimulation is initiated at a period of time during inspiration and is provided for a period a time in a manner configured to increase tidal volume. Stimulation during intrinsic breathing and augmenting breathing are described in one or more related applications as set forth herein which are incorporated completely and without limitation herein by reference. The tidal volume TV2 of the breaths 203, 204, 205 where inspiration is augmented is greater than the tidal volume TV1 of the intrinsic breaths 201, 202. According to one variation, the peak flow during stimulation Pf2 may be configured as shown to be close to the peak flow Pf1 during intrinsic breathing. The inspiration duration TI1 of intrinsic breathing is shorter than the inspiration duration TI2 of augmented breaths 203, 204, 205. The duration TD1 of intrinsic breathing is increased to duration TD2 and with stimulation signals 213 214, 215, to achieve a desired rate.

In accordance with another aspect of the invention, stimulation during intrinsic breathing may be provided to inhibit or delay onset of next inspiration. According to an aspect, stimulation may be provided during exhalation to inhibit or delay onset of an inspiration thereby slowing breathing rate. According to an aspect, stimulation may be provided to extend exhalation thereby delaying the onset of a subsequent inspiration. According to an aspect, stimulation may be provided at a low energy, low level or low frequency to inhibit onset of an inspiration, thereby slowing breathing rate. Examples of low energy, low level and/or low frequency stimulation are set forth in the related applications herein.

The rate of intrinsic breathing may be controlled by delaying intrinsic breaths with low energy (for example a lower amplitude, frequency and/or pulse width than desired for paced breathing) diaphragm stimulation provided during intrinsic breathing.

According to one aspect, low energy stimulation may be provided during intrinsic breathing, delaying onset of the next breath and thereby slowing breathing rate. According to another aspect, stimulation may be initiated sufficiently prior to the onset of the next breath so as to reduce the likelihood that the stimulation would trigger a breath. A combination of lower energy stimulation and timing the stimulation sufficiently prior to the onset of the next breath may be used to slow breathing rate.

FIGS. 3A to 3D illustrate stimulation provided to slow breathing in accordance with one aspect of the invention. FIG. 3A illustrates intrinsic diaphragm EMG activity corresponding to breaths 301 through 307. FIGS. 3B and 3C respectively illustrate flow and tidal volume corresponding to breaths 301 through 307. FIG. 3D illustrates stimulation envelopes corresponding to stimulation signals 313, 314, 315, 316, and 317 provided prior to onset of breaths 303, 304, 305, 306, and 307 respectively. Stimulation 313, 314, 315, 316, 317 is provided prior to the onset of breath 303, 304, 305, 306, 307 respectively, as determined, for example, by a model that predicts the onset of breathing or by the actual detection of the intrinsic diaphragm EMG activity (FIG. 3A). Stimulation is sustained for a period of time. For example, the stimulation may be provided until the onset of the intrinsic breath is detected by the EMG or other physiological signals. As illustrated, the stimulation increases the duration of a respiration cycle T2 with respect to the duration T1 of an intrinsic breathing cycle. As further illustrated, intrinsic breathing cycles 303 to 307 may have greater flow or tidal volume to compensate for the slower breathing rate that is induced by the stimulation.

In accordance with another aspect of the invention, stimulation to increase tidal volume or inspiration duration may be provided in combination with stimulation during exhalation to inhibit or delay the onset of the next inspiration.

In accordance with another aspect of the invention stimulation may be provided to delay exhalation by stimulating at the end of inspiration at a level that slows exhalation. Such stimulation may be provided by stimulating during intrinsic breathing or by providing paced breathing for example that maintains minute ventilation while providing a slower rate of breathing.

FIGS. 4A-4C illustrate stimulation during intrinsic breathing in accordance with one aspect of the invention. FIG. 4A illustrates flow for breaths 401, 402, 403, 404 and 405. FIG. 4B illustrates tidal volume of breaths 401, 402, 403, 404 and 405. Breaths 401, 402 are intrinsic breaths. Breaths 403, 404, and 405 are intrinsic breaths that are augmented by stimulation configured to elicit a diaphragm response as illustrated schematically by stimulation markers 413, 414, and 415. Stimulation is initiated at a period of time at the end of inspiration and is provided for a period a time through the exhalation period. Detection and stimulation techniques are set forth, for example in related applications hereto. Stimulation may be provided at a low energy level including at a low frequency. Stimulation during intrinsic breathing and augmenting breathing, low level and/or low frequency are described in one or more related applications as set forth herein which are incorporated completely and without limitation herein by reference. The peak flow during stimulation Pfb may be greater than the peak flow Pfa during intrinsic breaths 401, 402 as illustrated. The peak flow during stimulation Pfb may be also not be greater than the peak flow Pfa during intrinsic breaths 401, 402. Similarly tidal volume Tb is for breaths 404, 405 after stimulation 413 and 414 respectively. Such greater flow or tidal volume may intrinsically compensate for the slower breathing rate that is induced by the stimulation. It is believed that stimulation during exhalation inhibits or delays onset of inspiration. The stimulation also slows exhalation (i.e., during the period which exhalation is occurring at a relatively faster rate) so that the exhalation duration TEb during stimulation is greater than the intrinsic exhalation duration TEa. Exhalation is slowed by stimulation thus slowing the overall rate of breathing. The duration of the intrinsic breathing respiration cycle TDa is increased to duration TDb during stimulation, thus reducing the breathing rate to a desired rate.

Stimulation may also be provided to slow or control breathing rate in a manner that provides a paced breath with controlled exhalation as illustrated for example in U.S. patent application Ser. No. 10/966,474, filed Oct. 15, 2004 and U.S. patent application Ser. No. 10/966,472, filed on Oct. 15, 2004.

FIGS. 5A to 5C illustrate stimulation used to control breathing and breathing rate in accordance with the invention. Breaths 501 and 502 are intrinsic breaths occurring at a rate such that the duration of the respiration cycle is TDi and having tidal volume TVi and peak flow PFi. Breaths 503, 504 and 505 are paced breaths with higher tidal volume TVp and peak flow PFp. Peak flow PFp may be controlled to be at a level substantially the same as, higher, or lower than intrinsic peak flow. Paced breathing is provided in a manner in which breathing is controlled or taken over by stimulated breathing. Examples of techniques for controlling breathing, respiratory drive and/or taking over breathing are set forth in related applications incorporated completely and without limitation herein by reference. In general greater tidal volume permits a reduction in breathing rate or an increase in duration of breathing cycle to TDii while maintaining minute ventilation. FIG. 5C illustrates stimulation envelopes 513, 514, 515 respectively corresponding to stimulated breaths 503, 504, 505.

In accordance with another aspect of the invention stimulation is provided to control minute ventilation to therapeutically affect blood gas levels. Examples of controlling minute ventilation are set forth for example in U.S. patent application Ser. No. 10/966,474. Such stimulation may be provided, for example, during sleep to thereby increase or normalize SaO2 levels during sleep. In accordance with one aspect of the invention minute ventilation is controlled to normalize SaO2 levels while not decreasing PaCO2 levels close to the apneic threshold. According to this aspect minute ventilation may be actively controlled using sensors to sense SaO2 or PaCO2 levels. Weaning off of pacing may be desirable to insure that the intrinsic drive to breath is still present. Paced breathing may be calibrated, for example at implant or adjusted during device use, so that the device is able to provide the appropriate minute ventilation at each pacing setting. This information may be obtained for example through sleep studies where the device is designed to provide stimulation during sleep.

In accordance with another aspect of the invention, stimulation is provided to create a deep inspiration or an increased tidal volume to thereby reduce sympathetic nerve bias, improve blood gas levels, stimulate reflexes (for example the Hering-Bruer reflex related to activating stretch receptors), increase lung volume, normalize or reset breathing (one or more parameters) or provide other beneficial therapies to improve cardiovascular function or heart failure condition.

Examples of creating deep inspiration are set forth in U.S. patent application Ser. No. 11/272,353 filed Nov. 10, 2005. While these examples refer to using deep inspiration to treat apnea, similar techniques for stimulation may be used to create deep inspiration breaths for improving cardiovascular function or treating heart failure. Stimulation may be provided during intrinsic inspiration or in between inspiration cycles.

In accordance with another aspect of the invention stimulation may be provided to manipulate intrathoracic pressure to thereby produce a therapeutic effect.

According to one embodiment, stimulation is provided to reduce intrathoracic pressure through induced contraction of the right and/or left hemidiaphragm. It is believed that for some patients, reduction in intrathoracic pressure may have a beneficial effect on the patient's cardiovascular function or condition. For example, a reduced intrathoracic pressure may increase stroke volume at least in part through a decrease in central venous pressure; and reduce pulmonary arterial and wedge pressures in relation to atmospheric. A reduced intrathoracic pressure may also provide a decrease in filling pressure in the right ventricle and may also thereby improve systemic venous return. A reduced intrathoracic pressure may also provide better coronary artery perfusion.

In accordance with one aspect of the invention, patients with heart failure manifesting in poor ventricular filling may be treated with stimulation to reduce intrathoracic pressure. In accordance with one aspect of the invention, patients with diastolic heart failure may be treated with stimulation to reduce intrathoracic pressure. In accordance with another aspect of the invention stimulation to reduce intrathoracic pressure may be provided to patients who are hypovolemic where the therapeutic effects of improved ventricular filling and venous return would be particularly beneficial.

According one aspect of the invention stimulation is provided to elicit a diaphragm response to cause a reduced intrathoracic pressure. The stimulation is provided at a level that does not elicit a breath, in other words, where intrinsic breathing continues to occur. Examples of stimulation such as bias stimulation and low energy or low frequency stimulation are described in related applications set forth herein. The stimulation eliciting a reduced intrathoracic pressure may be sustained or intermittent. Stimulation is preferably provided when a patient is sleeping but may also be provided when a patient is awake.

In accordance with one aspect of the invention, stimulation may be provided to one hemidiaphragm to elicit a more impactful change in intrathoracic pressure in the respective side of the thoracic cavity. For example the right hemidiaphragm may be stimulated in such a way to cause a reduced intrathoracic pressure primarily in the right thoracic cavity to thereby effect the right side of the heart to a greater degree than the left. Or stimulating unilaterally on the diaphragm may serve to minimize the pressure changes that the heart is exposed to. This may be beneficial when an increased lung volume is desired to treat OSA or CSA. Sensors may be used to sense arterial and venous blood volume so that stimulation may be adjusted based on patient's blood volume state. For example, stimulation may be increased or turned on when the patient is in a hypovolemic state where in a particular patient a greater benefit would be produced with a more negative intrathoracic pressure. Such sensors may include, for example, impedance (plethysmography) sensors used to monitor fluid levels in the body. Separate electrodes, or existing stimulation electrodes may be used in a configuration or with frequencies that can determine resistance and/or reactance. Fluid volume changes may, for example, be monitored based on a baseline established with the sensors and a hyper or hypo volemic state may be detected. A list of possible sensors are described in the references above.

In accordance with another aspect of the invention, stimulation is provided to elicit a diaphragm response that improves heart failure as described above in combination with treating sleep disorders that contribute to or worsen heart failure. Accordingly, stimulation is provided as described in the related patent applications set forth herein, to elicit a diaphragm response to thereby reduce breathing disorders to thereby improve condition of a heart failure patient. One or more specific methods of reducing sleep disordered breathing events and preventing sleep disordered breathing are described in related applications as set forth herein. In accordance with one aspect of the invention, stimulation is provided prior to a physiological trigger of a central or obstructive sleep apnea event in a manner that reduces the occurrence of such events, thus reducing the effects of apnea events that worsen heart failure.

In accordance with another aspect of the invention a combined cardiac rhythm management device and diaphragm/phrenic nerve stimulation device is provided to provide an enhanced combined treatment device. In accordance with this aspect of the invention, the diaphragm stimulation element may comprise an abdominally placed stimulator positioned on the diaphragm or phrenic nerve, a thoracoscopically placed stimulator positioned on the diaphragm or phrenic nerve, a phrenic nerve stimulator positioned in the neck region on or adjacent the phrenic nerve (transcutaneous, percutaneous, or otherwise implanted); transcutaneous stimulation of the diaphragm through leads at or near the ziphoid region (this may be in combination with a defibrillator function or device that is configured for subcutaneous stimulation of the heart); or a pectorally positioned lead, for example, placed transvenously in a vein or artery in proximity of one or both phrenic nerves.

The system may be further enhanced through the ability to avoid negative device/device interactions where a separate controller is used, e.g. for a CRT, pacemaker, ICD or other therapeutic electrical stimulation device. The system may also provide arrhythmia and sleep disorder detection algorithms through sensing of both the cardiac and respiration cycles.

The system may also be included in a combination with a CRM device having a common controller.

Additionally, the system may also be utilized to provide a continuous or synchronized low level stimulation to the phrenic nerve or diaphragm overlapped with the patient's own intrinsic breathing to reduce an intrathoracic pressure and improve cardiac output. The patient's SaO2 levels may also be improved and the heart and respiration rates may be reduced.

This may be achieved in part by sensing and/or monitoring the patient's intrathoracic pressure levels and applying the continuous or synchronized stimulation, as described herein, to reduce or alleviate the patient's elevated intrathoracic pressure. In applying the stimulation to the patient's phrenic nerve or diaphragm, any of the sensing and stimulation devices and methods described in the following may be utilized for applying the continuous or synchronized low level stimulation: U.S. Patent Application Ser. Nos. 61/893,404 filed Oct. 21, 2013; 60/925,024 filed Apr. 18, 2007; Ser. No. 13/598,284 filed Aug. 29, 2012; Ser. No. 12/082,057 filed Apr. 8, 2008; Ser. No. 12/082,057 filed Apr. 8, 2008; Ser. No. 12/069,823 filed Feb. 13, 2008; Ser. No. 12/044,932 filed Dec. 21, 2007; Ser. No. 11/981,342 filed Oct. 31, 2007; Ser. No. 11/480,074 filed Jun. 29, 2006; Ser. No. 11/271,315 filed Nov. 10, 2005; Ser. No. 11/271,554 filed Nov. 10, 2005; Ser. No. 11/271,353 filed Nov. 10, 2005; Ser. No. 11/271,264 filed Nov. 10, 2005; Ser. No. 11/480,074 filed Jun. 29, 2006;

Ser. No. 11/271,726 filed Nov. 10, 2005; Ser. No. 10/966,487 filed Oct. 15, 2004; Ser. No. 10/966,484 filed Oct. 15, 2004; Ser. No. 10/966,474, filed Oct. 15, 2004; Ser. No. 10/966,421 filed Oct. 15, 2004; Ser. No. 10/966,472 filed Oct. 15, 2004; Ser. No. 10/686,891 filed Oct. 15, 2003. Each of these applications is incorporated completely and without limitation herein by reference for any purpose.

Recent sensors and blood pressure and impedance sensing technologies have proven detecting worsening of heart failure as discussed in the Appendix below. The Appendix is incorporated herein by reference in its entirety for any purpose. A majority of these sensors monitor blood pressures within the pulmonary artery, right ventricle, left atrium, intrathoracic, or utilizing ventricular contractions or thoracic impedance to measure and monitor changes that could lead to heart hemodynamics decompensation or worsening and eventually hospitalization. These devices generally transmit a wireless signal through the sensor or a device that they are attached to the patient or caregiver for intervention that includes medication therapy or lifestyle or physician visit. However, none of these sensor technologies have offered a real-time therapy within the implantable device to improve cardiac output and also reduce intrathoracic, pulmonary, or cardiac pressures.

As described in the Appendix and herein, the implantable devices also include at least one phrenic nerve or diaphragm stimulation lead or electrodes to deliver therapy either reactively (in response to sensors and programmed parameters outcome) or proactively as determined duty cycle of a patient-induced event. Upon detection of an increase in pressures, the device may deliver stimulation in such a manner to reduce intrathoracic pressure and related pulmonary and cardiac pressures. Such therapy is expected to reduce pulmonary congestion and dyspnea in heart failure patients.

Another application of this device/technology is to improve cardiac hemodynamics by increasing venous return and cardiac output.

Another application of this technology includes applying negative pressure therapy even in the absence of increased pressures and to improve cardiac output and off-loading the heart. In the long-term, the heart could remodel and improve contractility on its own.

The implantable sensor could receive energy from outside the body such as the CardioMEMS pulmonary pressure sensor and then receive commands to stimulation phrenic nerve to reduce pressures and increase cardiac output. The stimulation electrodes could be also activated from outside the body.

Another application of this device is treating central and obstructive sleep apnea as described in further detail in the patent applications incorporated hereinabove.

Such devices could also synchronize its stimulation of the phrenic nerve to cardiac cycles such systole or diastole. However, in order to achieve sustained reduction in pulmonary or atrial pressures, a sustained stimulation that is synchronized to respiration cycles and also cardiac cycles may be provided. Intrathoracic pressure is lowest at the peak of inspiration and therefore while it is possible to stimulate, the stimulation applied toward the end of inspiration and/or part of or the entire exhalation phase may be more efficient.

The stimulation algorithm could be targeted toward multiple benefits/targets. At the time of device implant, the algorithms for each target could be titrated and thresholds could be established per patient:

1. Proactive stimulation during sleep or awake to increase cardiac output in diastolic or systolic heart failure patients;
    a. Device will self-adjust stimulation relative to the need for certain cardiac output increase;
2. Responsive therapy where the device monitors pressures or cardiac and intrathoracic impedances or cardiac output and therefore responds to need to reduce intrathoracic pressure;
3. Responsive device to increase cardiac output;
4. Responsive device to increase lung volume;
5. Integrated with any CRM device; pacemaker, defibrillator, cardiac resynchronization therapy (CRT);
6. Integrated with other heart failure devices such as vagal nerve stimulation or others;
7. Integrated with sleep apnea therapy devices including hypoglossal nerve stimulation devices.
8. Responsive therapy device to improve kidney function or improve GFR
9. Responsive device to reduce pulmonary pressures and pulmonary congestions In one example, because the algorithms for each target are able to be titrated, the phrenic nerve or diaphragm tissue may be stimulated to cause a titratable diaphragm contraction such that an initial pressure within a thoracic chamber is reduced. In another example, the phrenic nerve or diaphragm tissue may be stimulated to improve a cardiac output in titratable manner as well.

In stimulating the phrenic nerve or diaphragm as well as monitoring the patient's intrathoracic pressure, as described herein, the electrodes may be utilized in combination with or integral to a cardiac lead. Such electrodes are described in further detail in U.S. Patent Application Ser. No. 61/893,404 filed Oct. 21, 2013, which has been incorporated by reference hereinabove in its entirety and for any purpose.

The mapping and neurostimulation electrodes presented herein are intended to be used in conjunction with or integral to a cardiac lead. They could also be an independent lead. The mapping electrodes mounted on the sleeve is intended to traverse the cardiac lead, provide specificity to specific neural activation points within the vascular structure where neural anatomy resides adjacent to the vascular structure, such as the phrenic or vagus nerve. Once the targeted nerve anatomy is identified by the mapping electrodes, the neurostimulation electrodes can be arranged or deployed within the vascular structure and adjacent to the neural anatomy such that the electrodes provides the desired neurostimulation therapy.

Figure 6:
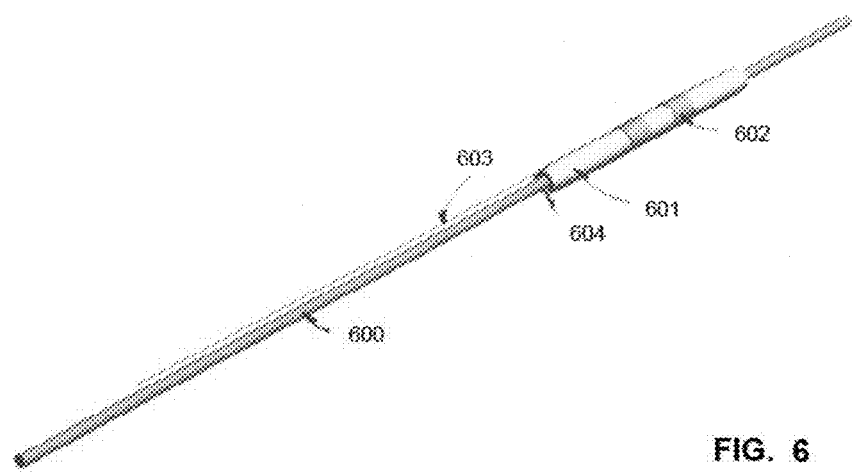
FIG. 6 is an isometric view of a mapping electrodes mounted on a mobile sleeve which is descending over a cardiac lead.

FIG. 6 illustrates an embodiment of a mapping sleeve 601 that includes at minimum one but in this embodiment plural mapping electrodes 602, traversing a cardiac lead 600. The mapping sleeve 601 in this embodiment is inserted over the cardiac lead 600 at the proximal end of the lead and advanced along the cardiac lead body to a position in which the mapping electrodes 602 are arranged to activate neural anatomy.

The mapping sleeve 601 may be constructed of a biostable polymer, silicone rubber, or other insulation materials suitable for isolating a plurality of electrodes. The mapping electrodes 602 may be constructed of platinum or platinum alloys but in other embodiments constructed of any biostable conductor, titanium, palladium, stainless steel, carbon, or similar materials, alloys. or composite materials.

Figure 7:
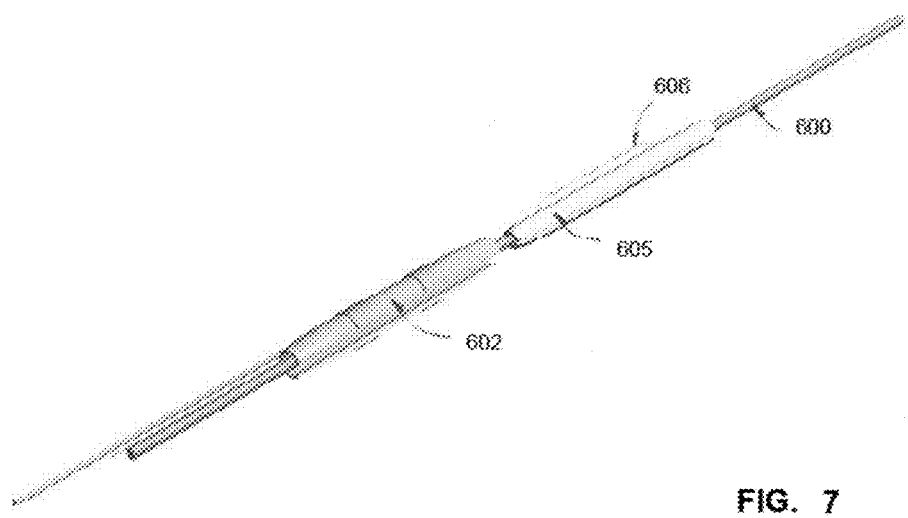
FIG. 7 is an isometric view of a mapping electrodes mounted on a mobile sleeve which is descending over a cardiac lead and includes deployed neuro-stimulation electrodes.

Once the neural anatomy is identified within the vascular structure, the mapping sleeve 601 is retracted as illustrated in FIG. 7 exposing an inner sleeve 605 that includes an expanding wire member 606. The wire member may be constructed of any bio-stable compliant metal, nitinol, stainless steel, titanium alloys, or plastic material suitable to expand into position.

Figure 8:
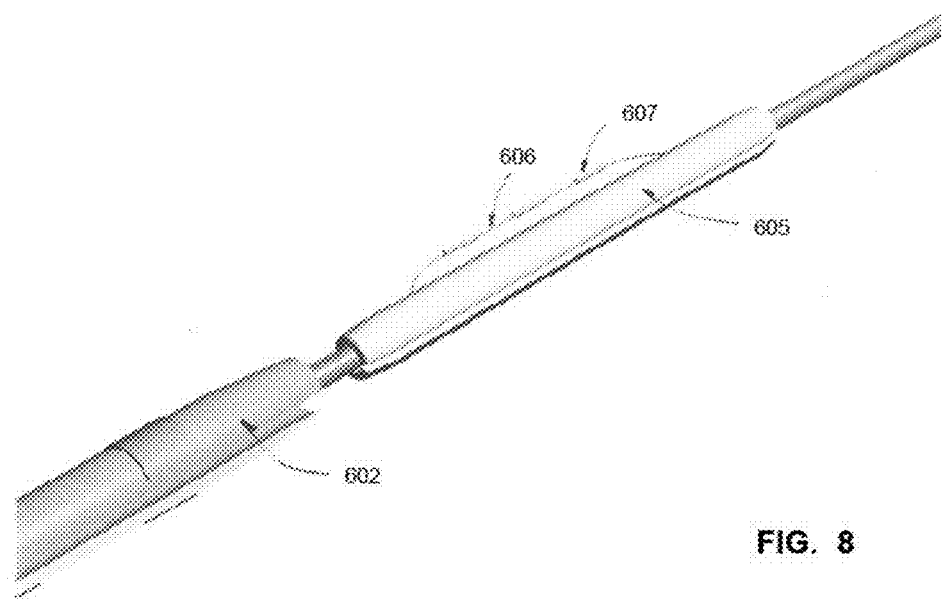
FIG. 8 is an enlarged isometric view of mapping electrodes mounted on a mobile sleeve including neuro-stimulating electrodes deployed on an expandable wire member.
Figure 9:
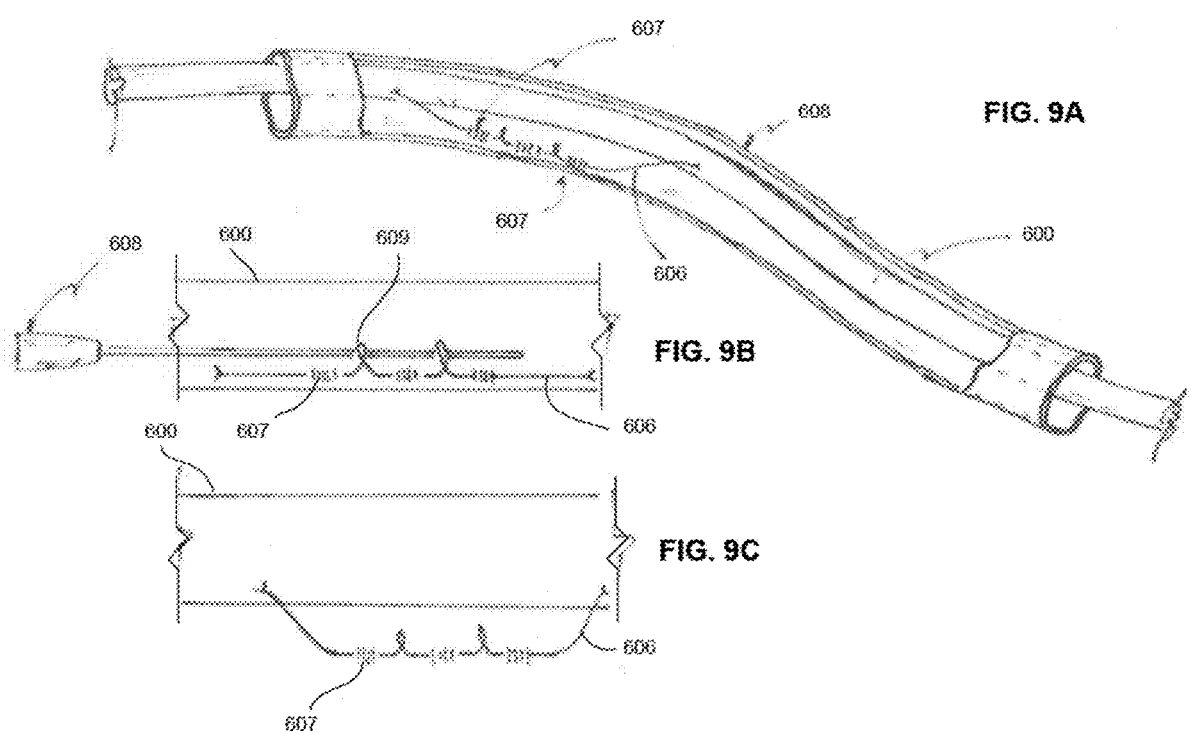
FIG. 9A is an exemplary side view of a neuro-stimulation electrode deployed, e.g., in a subclavian vein.
FIGS. 9B and 9C show detail side views of one mechanism for deploying the electrodes.

As illustrated in FIG. 8, the expanding wire member 606 in which carries at least one but in the preferred embodiment, plural neurostimulating electrodes 607. The expanding wire member 606 when in the un-deployed state, resides under the mapping sleeve so that the entire assembly can negotiate the vascular structure. The wire 606 may be retained in its low-profile configuration through various mechanism, such as a stylet 608 which may be passed through one or more retaining loops 609 defined along the wire 606, as shown in the detail view of FIG. 9B. When deployed, the stylet 608 may be retracted such that the expanding wire member 606 expands, as shown in the detail view of FIG. 9C, to apply the neurostimulation electrodes 607 against the vascular wall, as shown in FIG. 9A. In this example, the lead 600 may utilize a IS-1 type connector.

Figure 10:
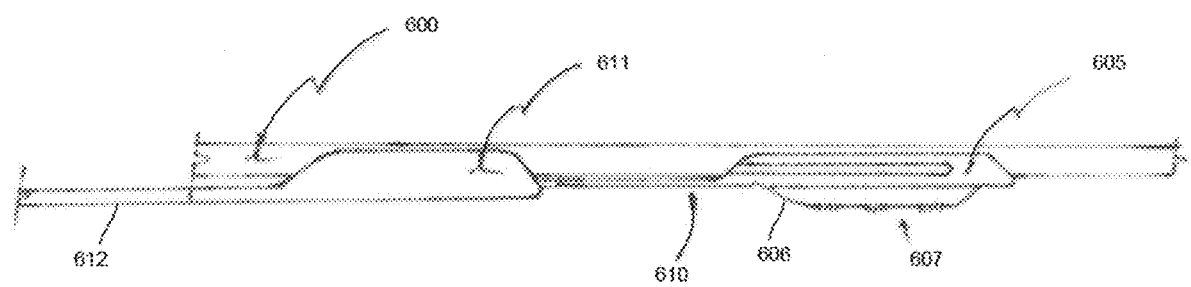
FIG. 10 is a detail side view of a neuro-stimulation electrode.

FIG. 10 illustrates an embodiment of the deployed neurostimulation electrodes 607 expanded to reside coincident to the vessel wall 608. In the primary embodiment, the electrode wire 606 containing the neurostimulation electrodes 607 have expanded to focus the electrodes 607 current towards the neural anatomy residing outside the vascular structure. In this variation, the electrode wire 606 and electrodes 607 may be attached or coupled to a conductor cable 610. A push sleeve 611 may be slidingly positioned proximally or distally of the electrode 607 with a proximal end of the push sleeve 611 being coupled to a push rod 612. During lead insertion and intravascular delivery, the pushing sleeve 611 may remain over the wire 606 and electrodes 607. When the electrodes 607 are in position relative to the tissue wall, the push rod 612 may be actuated proximally or distally relative to the lead 600 such that the push sleeve 611 is moved to expose the wire 606 and electrodes 607 which may then be deployed as the sleeve 611 is, e.g., retracted.

The mapping electrode may be advanced down a previously implanted cardiac lead body to a point in which neural structure intersects the vascular structure. The mapping electrode is used to identity "map" the optimal stimulation location or optimal location to place the neurostimulation electrodes within the vascular structure.

Once the optimal stimulation location is identified using the mapping electrodes, the neurostimulation electrodes are deployed such that the neurostimulation electrodes are positioned in a location to energize the targeted neural anatomy.

A method of mapping or identifying the nerve is developed where once the electrode is near proximity of the nerve, stimulations of variety of frequencies and amplitude will be applied in certain sequence for optimum nerve location. The physiological response to mapping procedure will be monitored and recorded. Once the electrode is in optimum location, the electrode location in reference to other anatomical landmarks are noted and the electrode is secured. In case of mapping the phrenic nerve, several physiological parameters including diaphragm movement and response, flow, tidal volume, lung volume, minute ventilation, upper airway muscle activity, and similar parameters as it relates to respiratory parameters will be monitored in order to identify the optimum electrode placement in reference to the phrenic nerve.

As a person skilled in the art will recognize from the previous detailed description and figures that modifications and changes may be made to the preferred embodiments of the invention without departing from the scope of this invention defined in the following claims.

I claim:

1. A method for reducing a renal pressure in a subject, comprising:
   sensing a physiologic parameter relating to cardiac function of a subject undergoing intrinsic respiration via one or multiple sensors positioned internally or externally within the patient;
   determining one or more hemodynamic parameters of the subject based on the physiologic parameter;
   determining a mean or average intrathoracic pressure based on the physiologic parameter; and
   stimulating a phrenic nerve or diaphragm of the subject at least during a portion of an exhalation and/or rest cycle to maintain the diaphragm contracted relative to a non-stimulated diaphragm during the exhalation and/or rest cycle over a sustained period of time via an electrode to increase a functional residual capacity of the subject such that the mean or average intrathoracic pressure is decreased and the renal pressure is correspondingly reduced to improve the one or more hemodynamic parameters.

2. The method of claim 1 wherein the sensing of the physiologic parameter comprises monitoring a cardiac output of the patient.

3. The method of claim 2 wherein the monitoring of the cardiac output comprises monitoring one or more of a pulmonary artery, right ventricle, left atrium, left ventricle pressures, cardiac contractility, and/or cardiac and intrathoracic impedances.

4. The method of claim 1 wherein the stimulating of the phrenic nerve or diaphragm comprises adjusting a stimulation applied to the phrenic nerve or diaphragm in response to the physiologic parameter such that an initial pressure within a thoracic chamber is reduced.

5. The method of claim 1 wherein the stimulating of the phrenic nerve or diaphragm comprises stimulating to improve a hemodynamic parameter of the heart.

6. The method of claim 1 wherein the stimulating of the phrenic nerve or diaphragm comprises adjusting a stimulation applied to the phrenic nerve or diaphragm in response to the physiologic parameter to improve a cardiac output.

7. The method of claim 1 wherein the stimulating of the phrenic nerve or diaphragm comprises stimulating in an acute or chronic setting.

8. The method of claim 1 wherein the stimulating of the phrenic nerve or diaphragm comprises decreasing a right atrial pressure and improving kidney filtration.

9. The method of claim 1 wherein the stimulating of the phrenic nerve or diaphragm comprises reducing a cardiac filling pressure to reduce the renal pressure.

10. The method of claim 1 wherein the stimulating of the phrenic nerve or diaphragm comprises modulating or manipulating the intrathoracic pressure to activate renal sympathetic activity.

11. The method of claim 1 wherein the stimulating of the phrenic nerve or diaphragm comprises modulating or manipulating the intrathoracic pressure to activate renal sympathetic activity such that a kidney glomerular filtration rate (GFR) is increased.

12. The method of claim 1 wherein stimulating the phrenic nerve or diaphragm comprises reducing a sympathetic efferent outflow to a heart of the patient such that norepinephrine spillover is reduced.

13. A device for reducing a renal pressure in a patient, comprising:
   at least one electrode in electrical communication with a diaphragm or phrenic nerve tissue of a patient's body, wherein the at least one electrode or a second electrode is configured for sensing a physiologic parameter relating to the patient's hemodynamics; and, a control unit in electrical communication with the at least one electrode, wherein the control unit is programmed to generate an electrical stimulation signal in response to a sensed hemodynamic parameter and deliver the electrical stimulation signal through the at least one electrode at least during a portion of an exhalation and/or rest cycle to maintain the diaphragm contracted relative to a non-stimulated diaphragm during the exhalation and/or rest cycle over a sustained period of time to the diaphragm or phrenic nerve tissue to increase a functional residual capacity of the patient undergoing intrinsic respiration, wherein the control unit is further programmed to deliver the electrical stimulation signal until a mean or average intrathoracic pressure as determined by the control unit and based upon the physiologic parameter is decreased and a renal pressure is correspondingly reduced.

14. The device of claim 13 wherein the control unit is programmed to sense a cardiac related parameter of the patient.

15. The device of claim 13 wherein the control unit is programmed to deliver the electrical stimulation signal to cause a titratable diaphragm contraction such that an initial pressure within a thoracic chamber is reduced.

16. The device of claim 13 wherein the control unit is programmed to deliver the electrical stimulation signal to improve a hemodynamic parameter of the heart.

17. The device of claim 13 wherein the control unit is programmed to adjust the electrical stimulation signal in response to the physiologic parameter to improve a cardiac output.

18. The device of claim 13 wherein the control unit is programmed to deliver the electrical stimulation signal to decrease a right atrial pressure and improve kidney filtration.

19. The device of claim 13 wherein the control unit is programmed to deliver the electrical stimulation signal to reduce a cardiac filling pressure to reduce the renal pressure.

20. The device of claim 13 wherein the control unit is programmed to deliver the electrical stimulation signal to modulate or manipulate the intrathoracic pressure to activate renal sympathetic activity.

21. The device of claim 13 wherein the control unit is programmed to deliver the electrical stimulation signal to modulate or manipulate the intrathoracic pressure to activate renal sympathetic activity such that a kidney glomerular filtration rate (GFR) is increased.

22. The device of claim 13 wherein the control unit is programmed to deliver the electrical stimulation signal to reduce a sympathetic efferent outflow to a heart of the patient such that norepinephrine spillover is reduced.

* * * * *